US012767715B2

(12) United States Patent
Li

(10) Patent No.: US 12,767,715 B2
(45) Date of Patent: Oct. 20, 2026

(54) SINGLE-DOMAIN ANTIBODY TARGETING PD-1, DERIVATIVE THEREOF AND USE THEREOF

(71) Applicant: LILING BIOPHARMACEUTICALS CO., LTD., Suzhou (CN)

(72) Inventor: Yujun Li, Suzhou (CN)

(73) Assignee: LILING BIOPHARMACEUTICALS CO., LTD., Suzhou (CN)

( * ) Notice: Subject to any disclaimer, the term of this patent is extended or adjusted under 35 U.S.C. 154(b) by 588 days.

(21) Appl. No.: 18/261,450

(22) PCT Filed: Jan. 13, 2022

(86) PCT No.: PCT/CN2022/071865

§ 371 (c)(1),
(2) Date: Jul. 13, 2023

(87) PCT Pub. No.: WO2022/152222

PCT Pub. Date: Jul. 21, 2022

(65) Prior Publication Data

US 2025/0326845 A1 Oct. 23, 2025

(30) Foreign Application Priority Data

Jan. 14, 2021 (CN) ......................... 202110048196.1
Mar. 30, 2021 (CN) ......................... 202110343322.6

(51) Int. Cl.
*A61K 39/00* (2006.01)
*A61P 35/00* (2006.01)
*C07K 16/28* (2006.01)

(52) U.S. Cl.
CPC .......... *C07K 16/2818* (2013.01); *A61P 35/00* (2018.01); *A61K 2039/505* (2013.01); *C07K 2317/24* (2013.01); *C07K 2317/52* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2019/0191103 A1 6/2019 Takahashi et al.
2021/0261667 A1 8/2021 Wan et al.

FOREIGN PATENT DOCUMENTS

CN 108285485 A 7/2018
CN 110003336 A 7/2019
WO 2017020802 A1 2/2017
WO 2019137541 A1 7/2019
WO 2019158113 A1 8/2019
WO 2020077257 A1 4/2020
WO 2020127367 A1 6/2020

OTHER PUBLICATIONS

International Search Report for PCT/CN2022/071865 mailed Apr. 14, 2022, English Translation and Chinese version, 10 pages.
Office Action issued in Chinese Application No. 202110343322.6, mailed Nov. 23, 2022, with English translation.
Decision to Grant issued Chinese Application No. 202110343322.6, mailed Jan. 9, 2023, with English translation.
Corrected Decision to Grant issued Chinese Application No. 202110343322.6, mailed Jan. 16, 2023, with English translation.
Wu Zhen. Chordoma: Wu Zhen's Perspectives (2020). Beijing: Scientific and Technical Documentation Press, 2020, with English translation of the relevant part on p. 56, cited in Chinese Office Action, 154 pages provided.

*Primary Examiner* — Michail A Belyavskyi
(74) *Attorney, Agent, or Firm* — HSML P.C.

(57) ABSTRACT

Disclosed in the present invention are a single-domain antibody targeting human programmed cell death factor PD-1, and a humanized variant thereof. The VHH chain comprises CDR1 as shown in SEQ ID NO: 2, CDR2 as shown in SEQ ID NO: 3 and CDR3 as shown in SEQ ID NO: 4. The single-domain antibody targeting PD-1 of the present invention is capable of blocking interaction between PD-1 and PD-L1, thus has wide biological application value and clinical application value, and lays a new material foundation for the development of a therapeutic or diagnostic drug targeting PD-1.

12 Claims, 2 Drawing Sheets

Specification includes a Sequence Listing.

SEQUENCE LISTING

```
<160> NUMBER OF SEQ ID NOS: 37

<210> SEQ ID NO 1
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 1

Gln Leu Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ser Met Tyr
            20                  25                  30

Ala Met Gly Trp Phe Arg Gln Ser Pro Gly Asn Glu Arg Glu Phe Val
        35                  40                  45

Ala Gly Ile Gly Trp Glu Asn Asn Thr Pro Tyr Tyr Ala Arg Ser Val
    50                  55                  60

Glu Gly Arg Phe Thr Ile Ser Arg Asp Asn Val Lys Asn Thr Val Phe
65                  70                  75                  80

Leu Gln Met Asn Arg Leu Lys Pro Glu Asp Ala Ala Val Tyr Phe Cys
                85                  90                  95

Ala Ala Gln Ile Gly Ile Ser Gly Thr Leu Gly Asp Tyr Trp Gly Gln
            100                 105                 110

Gly Thr Gln Val Thr Val Ser Ser
        115                 120


<210> SEQ ID NO 2
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 2

Gly Arg Thr Ser Ser Met Tyr Ala Met Gly
1               5                   10


<210> SEQ ID NO 3
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 3

Gly Ile Gly Trp Glu Asn Asn Thr Pro Tyr Tyr Ala Arg Ser Val Glu
1               5                   10                  15

Gly Ser Glu Gln Ile Asp
```

20

<210> SEQ ID NO 4
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 4

Gln Ile Gly Ile Ser Gly Thr Leu Gly Asp Tyr
1 5 10

<210> SEQ ID NO 5
<211> LENGTH: 360
<212> TYPE: DNA
<213> ORGANISM: Artificial sequence
<220> FEATURE:
<223> OTHER INFORMATION: Synthetic polynucleotide

<400> SEQUENCE: 5
cagttgcagc tcgtggagtc gggaggaggg ctggtgcagg ctgggggctc tctgagactc 60
tcctgtgcag cctctggacg cacctccagt atgtatgcca tgggctggtt ccgccagtct 120
ccagggaacg agcgcgagtt tgtagcgggg attggctggg agaataatac cccatactat 180
gcacgctccg tggagggccg attcaccatc tccagagaca acgtcaagaa cacggtcttt 240
ctacaaatga acagactgaa acctgaggac gcggccgttt atttttgtgc agcccaaatc 300
ggaatatccg gtacattggg ggactactgg ggccagggga cccaggtcac cgtctcctca 360

<210> SEQ ID NO 6
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 6
ggacgcacct ccagtatgta tgccatgggc 30

<210> SEQ ID NO 7
<211> LENGTH: 51
<212> TYPE: DNA
<213> ORGANISM: Artificial sequence
<220> FEATURE:
<223> OTHER INFORMATION: Synthetic polynucleotide

<400> SEQUENCE: 7
gggattggct gggagaataa taccccatac tatgcacgct ccgtggaggg c 51

<210> SEQ ID NO 8
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 8
caaatcggaa tatccggtac attgggggac tac 33

<210> SEQ ID NO 9
<211> LENGTH: 229
<212> TYPE: PRT
<213> ORGANISM: Artificial sequence
<220> FEATURE:

<223> OTHER INFORMATION: Synthetic polypeptide

<400> SEQUENCE: 9

Glu Ser Lys Tyr Gly Pro Pro Cys Pro Pro Cys Pro Ala Pro Glu Phe
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys
225

<210> SEQ ID NO 10
<211> LENGTH: 1047
<212> TYPE: DNA
<213> ORGANISM: Artificial sequence
<220> FEATURE:
<223> OTHER INFORMATION: Synthetic polynucleotide

<400> SEQUENCE: 10
cagttgcagc tcgtggagtc gggaggaggg ctggtgcagg ctgggggctc tctgagactc 60
tcctgtgcag cctctggacg cacctccagt atgtatgcca tgggctggtt ccgccagtct 120
ccagggaacg agcgcgagtt tgtagcgggg attggctggg agaataatac cccatactat 180
gcacgctccg tggagggccg attcaccatc tccagagaca acgtcaagaa cacggtcttt 240
ctacaaatga acagactgaa acctgaggac gcggccgttt atttttgtgc agcccaaatc 300
ggaatatccg gtacattggg ggactactgg ggccagggga cccaggtcac cgtctcctca 360
gagtccaaat atggtccccc atgcccacca tgcccagcac ctgagttcct ggggggacca 420
tcagtcttcc tgttcccccc aaaacccaag gacactctca tgatctcccg gacccctgag 480
gtcacgtgcg tggtggtgga cgtgagccag gaagaccccg aggtccagtt caactggtac 540
gtggatggcg tggaggtgca taatgccaag acaaagccgc gggaggagca gttcaacagc 600

-continued

```
acgtaccgtg tggtcagcgt cctcaccgtc ctgcaccagg actggctgaa cggcaaggag    660

tacaagtgca aggtctccaa caaaggcctc ccgtcctcca tcgagaaaac catctccaaa    720

gccaaagggc agccccgaga gccacaggtg tacaccctgc ccccatccca ggaggagatg    780

accaagaacc aggtcagcct gacctgcctg gtcaaaggct tctaccccag cgacatcgcc    840

gtggagtggg agagcaatgg gcagccggag aacaactaca agaccacgcc tcccgtgctg    900

gactccgacg gctccttctt cctctacagc aggctaaccg tggacaagag caggtggcag    960

gaggggaatg tcttctcatg ctccgtgatg catgaggctc tgcacaacca ctacacacag   1020

aagagcctct ccctgtctct gggtaaa                                       1047


<210> SEQ ID NO 11
<211> LENGTH: 349
<212> TYPE: PRT
<213> ORGANISM: Artificial sequence
<220> FEATURE:
<223> OTHER INFORMATION: Synthetic polypeptide

<400> SEQUENCE: 11

Gln Leu Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ser Met Tyr
            20                  25                  30

Ala Met Gly Trp Phe Arg Gln Ser Pro Gly Asn Glu Arg Glu Phe Val
        35                  40                  45

Ala Gly Ile Gly Trp Glu Asn Asn Thr Pro Tyr Tyr Ala Arg Ser Val
    50                  55                  60

Glu Gly Arg Phe Thr Ile Ser Arg Asp Asn Val Lys Asn Thr Val Phe
65                  70                  75                  80

Leu Gln Met Asn Arg Leu Lys Pro Glu Asp Ala Ala Val Tyr Phe Cys
                85                  90                  95

Ala Ala Gln Ile Gly Ile Ser Gly Thr Leu Gly Asp Tyr Trp Gly Gln
            100                 105                 110

Gly Thr Gln Val Thr Val Ser Ser Glu Ser Lys Tyr Gly Pro Pro Cys
        115                 120                 125

Pro Pro Cys Pro Ala Pro Glu Phe Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser Gln Glu Asp Pro Glu Val Gln
                165                 170                 175

Phe Asn Trp Tyr Val Asp Gly Val Glu Val His Asn Ala Lys Thr Lys
            180                 185                 190

Pro Arg Glu Glu Gln Phe Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Gly Leu Pro Ser Ser Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Gln Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285
```

Pro Glu Asn Asn Tyr Lys Thr Thr Pro Pro Val Leu Asp Ser Asp Gly
290 295 300

Ser Phe Phe Leu Tyr Ser Arg Leu Thr Val Asp Lys Ser Arg Trp Gln
305 310 315 320

Glu Gly Asn Val Phe Ser Cys Ser Val Met His Glu Ala Leu His Asn
325 330 335

His Tyr Thr Gln Lys Ser Leu Ser Leu Ser Leu Gly Lys
340 345

<210> SEQ ID NO 12
<211> LENGTH: 447
<212> TYPE: PRT
<213> ORGANISM: Artificial sequence
<220> FEATURE:
<223> OTHER INFORMATION: Synthetic polypeptide

<400> SEQUENCE: 12

Gln Val Gln Leu Val Gln Ser Gly Val Glu Val Lys Lys Pro Gly Ala
1 5 10 15

Ser Val Lys Val Ser Cys Lys Ala Ser Gly Tyr Thr Phe Thr Asn Tyr
20 25 30

Tyr Met Tyr Trp Val Arg Gln Ala Pro Gly Gln Gly Leu Glu Trp Met
35 40 45

Gly Gly Ile Asn Pro Ser Asn Gly Gly Thr Asn Phe Asn Glu Lys Phe
50 55 60

Lys Asn Arg Val Thr Leu Thr Thr Asp Ser Ser Thr Thr Thr Ala Tyr
65 70 75 80

Met Glu Leu Lys Ser Leu Gln Phe Asp Asp Thr Ala Val Tyr Tyr Cys
85 90 95

Ala Arg Arg Asp Tyr Arg Phe Asp Met Gly Phe Asp Tyr Trp Gly Gln
100 105 110

Gly Thr Thr Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys
435 440 445

<210> SEQ ID NO 13
<211> LENGTH: 218
<212> TYPE: PRT
<213> ORGANISM: Artificial sequence
<220> FEATURE:
<223> OTHER INFORMATION: Synthetic polypeptide

<400> SEQUENCE: 13

Glu Ile Val Leu Thr Gln Ser Pro Ala Thr Leu Ser Leu Ser Pro Gly
1 5 10 15

Glu Arg Ala Thr Leu Ser Cys Arg Ala Ser Lys Gly Val Ser Thr Ser
20 25 30

Gly Tyr Ser Tyr Leu His Trp Tyr Gln Gln Lys Pro Gly Gln Ala Pro
35 40 45

Arg Leu Leu Ile Tyr Leu Ala Ser Tyr Leu Glu Ser Gly Val Pro Ala
50 55 60

Arg Phe Ser Gly Ser Gly Ser Gly Thr Asp Phe Thr Leu Thr Ile Ser
65 70 75 80

Ser Leu Glu Pro Glu Asp Phe Ala Val Tyr Tyr Cys Gln His Ser Arg
85 90 95

Asp Leu Pro Leu Thr Phe Gly Gly Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 14
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ser Ser Met Tyr
            20                  25                  30

Ala Met Gly Trp Phe Arg Gln Ala Pro Gly Lys Gly Arg Glu Phe Val
        35                  40                  45

Ala Gly Ile Gly Trp Glu Asn Asn Thr Pro Tyr Tyr Ala Arg Ser Val
    50                  55                  60

Glu Gly Arg Phe Thr Ile Ser Arg Asp Asn Val Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Gln Ile Gly Ile Ser Gly Thr Leu Gly Asp Tyr Trp Gly Gln
            100                 105                 110

Gly Thr Gln Val Thr Val Ser Ser
        115                 120
```

<210> SEQ ID NO 15
<211> LENGTH: 360
<212> TYPE: DNA
<213> ORGANISM: Artificial sequence
<220> FEATURE:
<223> OTHER INFORMATION: Synthetic polynucleotide

<400> SEQUENCE: 15

```
gaggtgcagc ttgttgaaag tggtggaggt cttgttcaac caggggggctc cctcagactg     60

tcttgtgcgg cgagcgggcg gacatcctct atgtatgcga tgggttggtt ccgacaggcc    120

cccggtaaag gacgggagtt cgtagctggc atcggttggg aaaacaatac cccttattac    180

gcccggtctg ttgaaggtcg atttactata agtcgggaca atgtgaaaaa tactgtctat    240

ctccaaatga actctctgcg ggccgaagat acagcggtgt actattgtgc cgcccaaatt    300

ggaatcagcg gaacattggg tgattattgg ggccaaggta cgcaagttac agtctcctca    360
```

<210> SEQ ID NO 16
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ser Ser Met Tyr
            20                  25                  30

Ala Met Gly Trp Phe Arg Gln Ala Pro Gly Asn Glu Arg Glu Phe Val
        35                  40                  45

Ala Gly Ile Gly Trp Glu Asn Asn Thr Pro Tyr Tyr Ala Arg Ser Val
    50                  55                  60
```

```
Glu Gly Arg Phe Thr Ile Ser Arg Asp Asn Val Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Gln Ile Gly Ile Ser Gly Thr Leu Gly Asp Tyr Trp Gly Gln
            100                 105                 110

Gly Thr Gln Val Thr Val Ser Ser
        115                 120
```

<210> SEQ ID NO 17
<211> LENGTH: 360
<212> TYPE: DNA
<213> ORGANISM: Artificial sequence
<220> FEATURE:
<223> OTHER INFORMATION: Synthetic polynucleotide

<400> SEQUENCE: 17

```
gaagtccaac tggtcgaaag cggcggcggt ctcgtccaac ctggaggctc tcttaggttg      60

tcatgtgccg cctcaggcag aacatccagc atgtacgcaa tgggttggtt cagacaggct     120

ccggggaacg agcgagaatt cgtcgcggga ataggatggg agaacaacac cccatactac     180

gcacgcagtg tggaaggccg attcactatt agtcgggata atgttaaaaa cacggtctac     240

cttcaaatga actcccttcg cgcagaggat actgcagttt attattgcgc ggcccaaata     300

ggtataagtg gaacactcgg ggactactgg ggccagggaa cacaggtaac cgtatcatca     360
```

<210> SEQ ID NO 18
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ser Ser Met Tyr
            20                  25                  30

Ala Met Gly Trp Phe Arg Gln Ala Pro Gly Asn Glu Arg Glu Phe Val
        35                  40                  45

Ala Gly Ile Gly Trp Glu Asn Asn Thr Pro Tyr Tyr Ala Arg Ser Val
    50                  55                  60

Glu Gly Arg Phe Thr Ile Ser Arg Asp Asn Val Lys Asn Thr Val Phe
65                  70                  75                  80

Leu Gln Met Asn Arg Leu Arg Ala Glu Asp Thr Ala Val Tyr Tyr Cys
                85                  90                  95

Ala Ala Gln Ile Gly Ile Ser Gly Thr Leu Gly Asp Tyr Trp Gly Gln
            100                 105                 110

Gly Thr Gln Val Thr Val Ser Ser
        115                 120
```

<210> SEQ ID NO 19
<211> LENGTH: 360
<212> TYPE: DNA
<213> ORGANISM: Artificial sequence
<220> FEATURE:
<223> OTHER INFORMATION: Synthetic polynucleotide

<400> SEQUENCE: 19

```
gaggtccagt tggtagaaag tggtggtggg ttggtgcaac ccggtggctc attgaggctg      60
```

tcttgtgctg cgagtggcag gacatcctct atgtatgcga tgggatggtt ccgacaagct 120
ccaggaaacg agcgcgagtt cgtagccgga attggttggg aaaacaatac gccctattat 180
gcacggtctg tcgaggggag gttcactatc tcacgcgaca acgtcaagaa cacagtgttt 240
cttcagatga accgactccg ggcggaggat acggccgtat attattgcgc agcgcaaatc 300
ggtatatccg gcactcttgg tgactattgg ggccagggta cacaagtgac agtctcttca 360

<210> SEQ ID NO 20
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ser Ser Met Tyr
            20                  25                  30

Ala Met Gly Trp Phe Arg Gln Ala Pro Gly Asn Glu Arg Glu Phe Val
        35                  40                  45

Ala Gly Ile Gly Trp Glu Asn Asn Thr Pro Tyr Tyr Ala Arg Ser Val
    50                  55                  60

Glu Gly Arg Phe Thr Ile Ser Arg Asp Asn Val Lys Asn Thr Val Phe
65                  70                  75                  80

Leu Gln Met Asn Arg Leu Lys Pro Glu Asp Thr Ala Val Tyr Tyr Cys
                85                  90                  95

Ala Ala Gln Ile Gly Ile Ser Gly Thr Leu Gly Asp Tyr Trp Gly Gln
            100                 105                 110

Gly Thr Gln Val Thr Val Ser Ser
        115                 120

<210> SEQ ID NO 21
<211> LENGTH: 360
<212> TYPE: DNA
<213> ORGANISM: Artificial sequence
<220> FEATURE:
<223> OTHER INFORMATION: Synthetic polynucleotide

<400> SEQUENCE: 21
gaagtgcaac tcgtggagag cgggggcgga cttgtccaac cgggagggag tttgagactc 60
tcatgcgccg cctctggtag aactagcagc atgtacgcta tgggatggtt caggcaggct 120
ccagggaacg aacgagaatt cgttgcaggc ataggatggg aaaacaacac cccatattac 180
gctcggtccg tggaaggacg atttactata agccgggaca atgtaaaaaa tactgtcttt 240
ctccagatga ataggctcaa gccggaggat acagcagttt attattgcgc tgctcaaatt 300
gggattagcg ggaccctggg tgactattgg gggcagggaa cgcaagtgac tgtcagttct 360

<210> SEQ ID NO 22
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 22

Glu Leu Gln Leu Val Glu Ser Gly Gly Gly Leu Val Gln Ala Gly Gly
1               5                   10                  15

```
Ser Leu Arg Leu Ser Cys Ala Ala Ser Gly Arg Thr Ser Ser Met Tyr
            20                  25                  30

Ala Met Gly Trp Phe Arg Gln Ala Pro Gly Asn Glu Arg Glu Phe Val
        35                  40                  45

Ala Gly Ile Gly Trp Glu Asn Asn Thr Pro Tyr Tyr Ala Arg Ser Val
    50                  55                  60

Glu Gly Arg Phe Thr Ile Ser Arg Asp Asn Val Lys Asn Thr Val Phe
65                  70                  75                  80

Leu Gln Met Asn Arg Leu Lys Pro Glu Asp Thr Ala Val Tyr Tyr Cys
                85                  90                  95

Ala Ala Gln Ile Gly Ile Ser Gly Thr Leu Gly Asp Tyr Trp Gly Gln
            100                 105                 110

Gly Thr Gln Val Thr Val Ser Ser
        115                 120


<210> SEQ ID NO 23
<211> LENGTH: 360
<212> TYPE: DNA
<213> ORGANISM: Artificial sequence
<220> FEATURE:
<223> OTHER INFORMATION: Synthetic polynucleotide

<400> SEQUENCE: 23

gagttgcaac tggtggaaag tggtggcggg ttggttcagg caggcggttc ccttcgcctc      60

tcctgtgcgg cgagtggacg cacatcatcc atgtacgcaa tggggtggtt tcgacaagcc     120

cccggaaacg aacgcgaatt tgttgctggg attggatggg aaaacaatac gccgtactat     180

gcccggagcg tagaaggacg attcaccatt tccagggaca acgtcaaaaa cacggtcttc     240

ttgcaaatga accgcttgaa accagaggat accgcagtat actattgtgc tgcccagatc     300

ggcatatcag gcacactggg cgactattgg ggccaaggga cccaggtcac tgtatccagc     360


<210> SEQ ID NO 24
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 24

Glu Leu Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ser Met Tyr
            20                  25                  30

Ala Met Gly Trp Phe Arg Gln Ala Pro Gly Asn Glu Arg Glu Phe Val
        35                  40                  45

Ala Gly Ile Gly Trp Glu Asn Asn Thr Pro Tyr Tyr Ala Arg Ser Val
    50                  55                  60

Glu Gly Arg Phe Thr Ile Ser Arg Asp Asn Val Lys Asn Thr Val Phe
65                  70                  75                  80

Leu Gln Met Asn Arg Leu Lys Pro Glu Asp Ala Ala Val Tyr Phe Cys
                85                  90                  95

Ala Ala Gln Ile Gly Ile Ser Gly Thr Leu Gly Asp Tyr Trp Gly Gln
            100                 105                 110

Gly Thr Gln Val Thr Val Ser Ser
        115                 120
```

<210> SEQ ID NO 25
<211> LENGTH: 360
<212> TYPE: DNA
<213> ORGANISM: Artificial sequence
<220> FEATURE:
<223> OTHER INFORMATION: Synthetic polynucleotide

<400> SEQUENCE: 25
gaactgcaac tcgtagaatc tgggggtggc ttggtccagg ccgggggcag tctgcgactt 60
tcctgtgccg catcaggaag gacctccagc atgtatgcga tgggatggtt ccgacaagct 120
ccgggaaatg agcgcgagtt tgttgcggga attggctggg agaataacac gccctattat 180
gctcggtccg tagaggggag gttcactatc agccgagata atgtaaaaaa caccgtattc 240
ctccaaatga atcggttgaa accagaggac gcagcggtct acttttgcgc cgcgcaaatc 300
ggcataagcg gtacattggg ggattactgg ggtcaaggca cacaggtaac cgtctctagt 360

<210> SEQ ID NO 26
<211> LENGTH: 349
<212> TYPE: PRT
<213> ORGANISM: Artificial sequence
<220> FEATURE:
<223> OTHER INFORMATION: Synthetic polypeptide

<400> SEQUENCE: 26

Glu Val Gln Leu Val Glu Ser Gly Gly Gly Leu Val Gln Pro Gly Gly
1 5 10 15

Ser Leu Arg Leu Ser Cys Ala Ala Ser Gly Arg Thr Ser Ser Met Tyr
20 25 30

Ala Met Gly Trp Phe Arg Gln Ala Pro Gly Lys Gly Arg Glu Phe Val
35 40 45

Ala Gly Ile Gly Trp Glu Asn Asn Thr Pro Tyr Tyr Ala Arg Ser Val
50 55 60

Glu Gly Arg Phe Thr Ile Ser Arg Asp Asn Val Lys Asn Thr Val Tyr
65 70 75 80

Leu Gln Met Asn Ser Leu Arg Ala Glu Asp Thr Ala Val Tyr Tyr Cys
85 90 95

Ala Ala Gln Ile Gly Ile Ser Gly Thr Leu Gly Asp Tyr Trp Gly Gln
100 105 110

Gly Thr Gln Val Thr Val Ser Ser Glu Ser Lys Tyr Gly Pro Pro Cys
115 120 125

Pro Pro Cys Pro Ala Pro Glu Phe Leu Gly Gly Pro Ser Val Phe Leu
130 135 140

Phe Pro Pro Lys Pro Lys Asp Thr Leu Met Ile Ser Arg Thr Pro Glu
145 150 155 160

Val Thr Cys Val Val Val Asp Val Ser Gln Glu Asp Pro Glu Val Gln
165 170 175

Phe Asn Trp Tyr Val Asp Gly Val Glu Val His Asn Ala Lys Thr Lys
180 185 190

Pro Arg Glu Glu Gln Phe Asn Ser Thr Tyr Arg Val Val Ser Val Leu
195 200 205

Thr Val Leu His Gln Asp Trp Leu Asn Gly Lys Glu Tyr Lys Cys Lys
210 215 220

Val Ser Asn Lys Gly Leu Pro Ser Ser Ile Glu Lys Thr Ile Ser Lys
225 230 235 240

Ala Lys Gly Gln Pro Arg Glu Pro Gln Val Tyr Thr Leu Pro Pro Ser
245 250 255

```
Gln Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Arg Leu Thr Val Asp Lys Ser Arg Trp Gln
305                 310                 315                 320

Glu Gly Asn Val Phe Ser Cys Ser Val Met His Glu Ala Leu His Asn
                325                 330                 335

His Tyr Thr Gln Lys Ser Leu Ser Leu Ser Leu Gly Lys
            340                 345
```

<210> SEQ ID NO 27
<211> LENGTH: 1047
<212> TYPE: DNA
<213> ORGANISM: Artificial sequence
<220> FEATURE:
<223> OTHER INFORMATION: Synthetic polynucleotide

<400> SEQUENCE: 27

```
gaggtgcagc ttgttgaaag tggtggaggt cttgttcaac caggggggctc cctcagactg     60

tcttgtgcgg cgagcgggcg gacatcctct atgtatgcga tgggttggtt ccgacaggcc    120

cccggtaaag gacgggagtt cgtagctggc atcggttggg aaaacaatac cccttattac    180

gcccggtctg ttgaaggtcg atttactata agtcgggaca atgtgaaaaa tactgtctat    240

ctccaaatga actctctgcg ggccgaagat acagcggtgt actattgtgc cgcccaaatt    300

ggaatcagcg gaacattggg tgattattgg ggccaaggta cgcaagttac agtctcctca    360

gagtccaaat atggtccccc atgcccacca tgcccagcac ctgagttcct ggggggacca    420

tcagtcttcc tgttcccccc aaaacccaag gacactctca tgatctcccg gacccctgag    480

gtcacgtgcg tggtggtgga cgtgagccag gaagaccccg aggtccagtt caactggtac    540

gtggatggcg tggaggtgca taatgccaag acaaagccgc gggaggagca gttcaacagc    600

acgtaccgtg tggtcagcgt cctcaccgtc ctgcaccagg actggctgaa cggcaaggag    660

tacaagtgca aggtctccaa caaaggcctc ccgtcctcca tcgagaaaac catctccaaa    720

gccaaagggc agccccgaga gccacaggtg tacaccctgc ccccatccca ggaggagatg    780

accaagaacc aggtcagcct gacctgcctg gtcaaaggct tctaccccag cgacatcgcc    840

gtggagtggg agagcaatgg gcagccggag aacaactaca agaccacgcc tcccgtgctg    900

gactccgacg gctccttctt cctctacagc aggctaaccg tggacaagag caggtggcag    960

gaggggaatg tcttctcatg ctccgtgatg catgaggctc tgcacaacca ctacacacag   1020

aagagcctct ccctgtctct gggtaaa                                      1047
```

<210> SEQ ID NO 28
<211> LENGTH: 349
<212> TYPE: PRT
<213> ORGANISM: Artificial sequence
<220> FEATURE:
<223> OTHER INFORMATION: Synthetic polypeptide

<400> SEQUENCE: 28

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ser Ser Met Tyr
            20                  25                  30
```

```
Ala Met Gly Trp Phe Arg Gln Ala Pro Gly Asn Glu Arg Glu Phe Val
        35                  40                  45

Ala Gly Ile Gly Trp Glu Asn Asn Thr Pro Tyr Tyr Ala Arg Ser Val
    50                  55                  60

Glu Gly Arg Phe Thr Ile Ser Arg Asp Asn Val Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Gln Ile Gly Ile Ser Gly Thr Leu Gly Asp Tyr Trp Gly Gln
            100                 105                 110

Gly Thr Gln Val Thr Val Ser Ser Glu Ser Lys Tyr Gly Pro Pro Cys
        115                 120                 125

Pro Pro Cys Pro Ala Pro Glu Phe Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser Gln Glu Asp Pro Glu Val Gln
                165                 170                 175

Phe Asn Trp Tyr Val Asp Gly Val Glu Val His Asn Ala Lys Thr Lys
            180                 185                 190

Pro Arg Glu Glu Gln Phe Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Gly Leu Pro Ser Ser Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Gln Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Arg Leu Thr Val Asp Lys Ser Arg Trp Gln
305                 310                 315                 320

Glu Gly Asn Val Phe Ser Cys Ser Val Met His Glu Ala Leu His Asn
                325                 330                 335

His Tyr Thr Gln Lys Ser Leu Ser Leu Ser Leu Gly Lys
            340                 345
```

<210> SEQ ID NO 29
<211> LENGTH: 1047
<212> TYPE: DNA
<213> ORGANISM: Artificial sequence
<220> FEATURE:
<223> OTHER INFORMATION: Synthetic polynucleotide

<400> SEQUENCE: 29

```
gaagtccaac tggtcgaaag cggcggcggt ctcgtccaac ctggaggctc tcttaggttg     60

tcatgtgccg cctcaggcag aacatccagc atgtacgcaa tgggttggtt cagacaggct    120

ccggggaacg agcgagaatt cgtcgcggga ataggatggg agaacaacac cccatactac    180

gcacgcagtg tggaaggccg attcactatt agtcgggata atgttaaaaa cacggtctac    240
```

```
cttcaaatga actcccttcg cgcagaggat actgcagttt attattgcgc ggcccaaata    300

ggtataagtg gaacactcgg ggactactgg ggccagggaa cacaggtaac cgtatcatca    360

gagtccaaat atggtccccc atgcccacca tgcccagcac ctgagttcct gggggggacca    420

tcagtcttcc tgttcccccc aaaacccaag gacactctca tgatctcccg gacccctgag    480

gtcacgtgcg tggtggtgga cgtgagccag gaagaccccg aggtccagtt caactggtac    540

gtggatggcg tggaggtgca taatgccaag acaaagccgc gggaggagca gttcaacagc    600

acgtaccgtg tggtcagcgt cctcaccgtc ctgcaccagg actggctgaa cggcaaggag    660

tacaagtgca aggtctccaa caaaggcctc ccgtcctcca tcgagaaaac catctccaaa    720

gccaaagggc agccccgaga gccacaggtg tacaccctgc ccccatccca ggaggagatg    780

accaagaacc aggtcagcct gacctgcctg gtcaaaggct tctaccccag cgacatcgcc    840

gtggagtggg agagcaatgg gcagccggag aacaactaca agaccacgcc tcccgtgctg    900

gactccgacg gctccttctt cctctacagc aggctaaccg tggacaagag caggtggcag    960

gaggggaatg tcttctcatg ctccgtgatg catgaggctc tgcacaacca ctacacacag   1020

aagagcctct ccctgtctct gggtaaa                                       1047
```

```
<210> SEQ ID NO 30
<211> LENGTH: 349
<212> TYPE: PRT
<213> ORGANISM: Artificial sequence
<220> FEATURE:
<223> OTHER INFORMATION: Synthetic polypeptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ser Ser Met Tyr
            20                  25                  30

Ala Met Gly Trp Phe Arg Gln Ala Pro Gly Asn Glu Arg Glu Phe Val
        35                  40                  45

Ala Gly Ile Gly Trp Glu Asn Asn Thr Pro Tyr Tyr Ala Arg Ser Val
    50                  55                  60

Glu Gly Arg Phe Thr Ile Ser Arg Asp Asn Val Lys Asn Thr Val Phe
65                  70                  75                  80

Leu Gln Met Asn Arg Leu Arg Ala Glu Asp Thr Ala Val Tyr Tyr Cys
                85                  90                  95

Ala Ala Gln Ile Gly Ile Ser Gly Thr Leu Gly Asp Tyr Trp Gly Gln
            100                 105                 110

Gly Thr Gln Val Thr Val Ser Ser Glu Ser Lys Tyr Gly Pro Pro Cys
        115                 120                 125

Pro Pro Cys Pro Ala Pro Glu Phe Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser Gln Glu Asp Pro Glu Val Gln
                165                 170                 175

Phe Asn Trp Tyr Val Asp Gly Val Glu Val His Asn Ala Lys Thr Lys
            180                 185                 190

Pro Arg Glu Glu Gln Phe Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220
```

```
Val Ser Asn Lys Gly Leu Pro Ser Ser Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Gln Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Arg Leu Thr Val Asp Lys Ser Arg Trp Gln
305                 310                 315                 320

Glu Gly Asn Val Phe Ser Cys Ser Val Met His Glu Ala Leu His Asn
                325                 330                 335

His Tyr Thr Gln Lys Ser Leu Ser Leu Ser Leu Gly Lys
            340                 345
```

<210> SEQ ID NO 31
<211> LENGTH: 1047
<212> TYPE: DNA
<213> ORGANISM: Artificial sequence
<220> FEATURE:
<223> OTHER INFORMATION: Synthetic polynucleotide

<400> SEQUENCE: 31

```
gaggtccagt tggtagaaag tggtggtggg ttggtgcaac ccggtggctc attgaggctg     60

tcttgtgctg cgagtggcag gacatcctct atgtatgcga tgggatggtt ccgacaagct    120

ccaggaaacg agcgcgagtt cgtagccgga attggttggg aaaacaatac gccctattat    180

gcacggtctg tcgaggggag gttcactatc tcacgcgaca acgtcaagaa cacagtgttt    240

cttcagatga accgactccg ggcggaggat acggccgtat attattgcgc agcgcaaatc    300

ggtatatccg gcactcttgg tgactattgg ggccagggta cacaagtgac agtctcttca    360

gagtccaaat atggtccccc atgcccacca tgcccagcac ctgagttcct gggggggacca    420

tcagtcttcc tgttcccccc aaaacccaag gacactctca tgatctcccg gacccctgag    480

gtcacgtgcg tggtggtgga cgtgagccag gaagaccccg aggtccagtt caactggtac    540

gtggatggcg tggaggtgca taatgccaag acaaagccgc gggaggagca gttcaacagc    600

acgtaccgtg tggtcagcgt cctcaccgtc ctgcaccagg actggctgaa cggcaaggag    660

tacaagtgca aggtctccaa caaaggcctc ccgtcctcca tcgagaaaac catctccaaa    720

gccaaagggc agccccgaga gccacaggtg tacaccctgc ccccatccca ggaggagatg    780

accaagaacc aggtcagcct gacctgcctg gtcaaaggct tctaccccag cgacatcgcc    840

gtggagtggg agagcaatgg gcagccggag aacaactaca agaccacgcc tcccgtgctg    900

gactccgacg gctccttctt cctctacagc aggctaaccg tggacaagag caggtggcag    960

gaggggaatg tcttctcatg ctccgtgatg catgaggctc tgcacaacca ctacacacag   1020

aagagcctct ccctgtctct gggtaaa                                        1047
```

<210> SEQ ID NO 32
<211> LENGTH: 349
<212> TYPE: PRT
<213> ORGANISM: Artificial sequence
<220> FEATURE:
<223> OTHER INFORMATION: Synthetic polypeptide

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ser Ser Met Tyr
            20                  25                  30

Ala Met Gly Trp Phe Arg Gln Ala Pro Gly Asn Glu Arg Glu Phe Val
        35                  40                  45

Ala Gly Ile Gly Trp Glu Asn Asn Thr Pro Tyr Tyr Ala Arg Ser Val
    50                  55                  60

Glu Gly Arg Phe Thr Ile Ser Arg Asp Asn Val Lys Asn Thr Val Phe
65                  70                  75                  80

Leu Gln Met Asn Arg Leu Lys Pro Glu Asp Thr Ala Val Tyr Tyr Cys
                85                  90                  95

Ala Ala Gln Ile Gly Ile Ser Gly Thr Leu Gly Asp Tyr Trp Gly Gln
            100                 105                 110

Gly Thr Gln Val Thr Val Ser Ser Glu Ser Lys Tyr Gly Pro Pro Cys
        115                 120                 125

Pro Pro Cys Pro Ala Pro Glu Phe Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser Gln Glu Asp Pro Glu Val Gln
                165                 170                 175

Phe Asn Trp Tyr Val Asp Gly Val Glu Val His Asn Ala Lys Thr Lys
            180                 185                 190

Pro Arg Glu Glu Gln Phe Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Gly Leu Pro Ser Ser Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Gln Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Arg Leu Thr Val Asp Lys Ser Arg Trp Gln
305                 310                 315                 320

Glu Gly Asn Val Phe Ser Cys Ser Val Met His Glu Ala Leu His Asn
                325                 330                 335

His Tyr Thr Gln Lys Ser Leu Ser Leu Ser Leu Gly Lys
            340                 345
```

<210> SEQ ID NO 33
<211> LENGTH: 1047
<212> TYPE: DNA
<213> ORGANISM: Artificial sequence
<220> FEATURE:
<223> OTHER INFORMATION: Synthetic polynucleotide

<400> SEQUENCE: 33

```
gaagtgcaac tcgtggagag cgggggcgga cttgtccaac cgggagggag tttgagactc     60
```

```
tcatgcgccg cctctggtag aactagcagc atgtacgcta tgggatggtt caggcaggct    120

ccagggaacg aacgagaatt cgttgcaggc ataggatggg aaaacaacac cccatattac    180

gctcggtccg tggaaggacg atttactata agccgggaca atgtaaaaaa tactgtcttt    240

ctccagatga ataggctcaa gccggaggat acagcagttt attattgcgc tgctcaaatt    300

gggattagcg ggaccctggg tgactattgg gggcagggaa cgcaagtgac tgtcagttct    360

gagtccaaat atggtccccc atgcccacca tgcccagcac ctgagttcct gggggggacca    420

tcagtcttcc tgttcccccc aaaacccaag gacactctca tgatctcccg gacccctgag    480

gtcacgtgcg tggtggtgga cgtgagccag gaagaccccg aggtccagtt caactggtac    540

gtggatggcg tggaggtgca taatgccaag acaaagccgc gggaggagca gttcaacagc    600

acgtaccgtg tggtcagcgt cctcaccgtc ctgcaccagg actggctgaa cggcaaggag    660

tacaagtgca aggtctccaa caaaggcctc ccgtcctcca tcgagaaaac catctccaaa    720

gccaaagggc agccccgaga gccacaggtg tacaccctgc ccccatccca ggaggagatg    780

accaagaacc aggtcagcct gacctgcctg gtcaaaggct tctaccccag cgacatcgcc    840

gtggagtggg agagcaatgg gcagccggag aacaactaca agaccacgcc tcccgtgctg    900

gactccgacg gctccttctt cctctacagc aggctaaccg tggacaagag caggtggcag    960

gaggggaatg tcttctcatg ctccgtgatg catgaggctc tgcacaacca ctacacacag   1020

aagagcctct ccctgtctct gggtaaa                                       1047
```

<210> SEQ ID NO 34
<211> LENGTH: 349
<212> TYPE: PRT
<213> ORGANISM: Artificial sequence
<220> FEATURE:
<223> OTHER INFORMATION: Synthetic polypeptide

<400> SEQUENCE: 34

```
Glu Leu Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ser Met Tyr
            20                  25                  30

Ala Met Gly Trp Phe Arg Gln Ala Pro Gly Asn Glu Arg Glu Phe Val
        35                  40                  45

Ala Gly Ile Gly Trp Glu Asn Asn Thr Pro Tyr Tyr Ala Arg Ser Val
    50                  55                  60

Glu Gly Arg Phe Thr Ile Ser Arg Asp Asn Val Lys Asn Thr Val Phe
65                  70                  75                  80

Leu Gln Met Asn Arg Leu Lys Pro Glu Asp Thr Ala Val Tyr Tyr Cys
                85                  90                  95

Ala Ala Gln Ile Gly Ile Ser Gly Thr Leu Gly Asp Tyr Trp Gly Gln
            100                 105                 110

Gly Thr Gln Val Thr Val Ser Ser Glu Ser Lys Tyr Gly Pro Pro Cys
        115                 120                 125

Pro Pro Cys Pro Ala Pro Glu Phe Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser Gln Glu Asp Pro Glu Val Gln
                165                 170                 175

Phe Asn Trp Tyr Val Asp Gly Val Glu Val His Asn Ala Lys Thr Lys
```

```
            180                 185                 190

Pro Arg Glu Glu Gln Phe Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Gly Leu Pro Ser Ser Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Gln Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Arg Leu Thr Val Asp Lys Ser Arg Trp Gln
305                 310                 315                 320

Glu Gly Asn Val Phe Ser Cys Ser Val Met His Glu Ala Leu His Asn
                325                 330                 335

His Tyr Thr Gln Lys Ser Leu Ser Leu Ser Leu Gly Lys
            340                 345


<210> SEQ ID NO 35
<211> LENGTH: 1047
<212> TYPE: DNA
<213> ORGANISM: Artificial sequence
<220> FEATURE:
<223> OTHER INFORMATION: Synthetic polynucleotide

<400> SEQUENCE: 35

gagttgcaac tggtggaaag tggtggcggg ttggttcagg caggcggttc ccttcgcctc      60

tcctgtgcgg cgagtggacg cacatcatcc atgtacgcaa tggggtggtt tcgacaagcc     120

cccggaaacg aacgcgaatt tgttgctggg attggatggg aaaacaatac gccgtactat     180

gcccggagcg tagaaggacg attcaccatt tccagggaca acgtcaaaaa cacggtcttc     240

ttgcaaatga accgcttgaa accagaggat accgcagtat actattgtgc tgcccagatc     300

ggcatatcag gcacactggg cgactattgg ggccaaggga cccaggtcac tgtatccagc     360

gagtccaaat atggtccccc atgcccacca tgcccagcac ctgagttcct gggggggacca    420

tcagtcttcc tgttcccccc aaaacccaag gacactctca tgatctcccg gacccctgag     480

gtcacgtgcg tggtggtgga cgtgagccag gaagaccccg aggtccagtt caactggtac     540

gtggatggcg tggaggtgca taatgccaag acaaagccgc gggaggagca gttcaacagc     600

acgtaccgtg tggtcagcgt cctcaccgtc ctgcaccagg actggctgaa cggcaaggag     660

tacaagtgca aggtctccaa caaaggcctc ccgtcctcca tcgagaaaac catctccaaa     720

gccaaagggc agccccgaga gccacaggtg tacaccctgc ccccatccca ggaggagatg     780

accaagaacc aggtcagcct gacctgcctg gtcaaaggct tctaccccag cgacatcgcc     840

gtggagtggg agagcaatgg gcagccggag aacaactaca agaccacgcc tcccgtgctg     900

gactccgacg gctccttctt cctctacagc aggctaaccg tggacaagag caggtggcag     960

gaggggaatg tcttctcatg ctccgtgatg catgaggctc tgcacaacca ctacacacag    1020

aagagcctct ccctgtctct gggtaaa                                        1047
```

<210> SEQ ID NO 36
<211> LENGTH: 349
<212> TYPE: PRT
<213> ORGANISM: Artificial sequence
<220> FEATURE:
<223> OTHER INFORMATION: Synthetic polypeptide

<400> SEQUENCE: 36

```
Glu Leu Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ser Met Tyr
            20                  25                  30

Ala Met Gly Trp Phe Arg Gln Ala Pro Gly Asn Glu Arg Glu Phe Val
        35                  40                  45

Ala Gly Ile Gly Trp Glu Asn Asn Thr Pro Tyr Tyr Ala Arg Ser Val
    50                  55                  60

Glu Gly Arg Phe Thr Ile Ser Arg Asp Asn Val Lys Asn Thr Val Phe
65                  70                  75                  80

Leu Gln Met Asn Arg Leu Lys Pro Glu Asp Ala Ala Val Tyr Phe Cys
                85                  90                  95

Ala Ala Gln Ile Gly Ile Ser Gly Thr Leu Gly Asp Tyr Trp Gly Gln
            100                 105                 110

Gly Thr Gln Val Thr Val Ser Ser Glu Ser Lys Tyr Gly Pro Pro Cys
        115                 120                 125

Pro Pro Cys Pro Ala Pro Glu Phe Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser Gln Glu Asp Pro Glu Val Gln
                165                 170                 175

Phe Asn Trp Tyr Val Asp Gly Val Glu Val His Asn Ala Lys Thr Lys
            180                 185                 190

Pro Arg Glu Glu Gln Phe Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Gly Leu Pro Ser Ser Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Gln Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Arg Leu Thr Val Asp Lys Ser Arg Trp Gln
305                 310                 315                 320

Glu Gly Asn Val Phe Ser Cys Ser Val Met His Glu Ala Leu His Asn
                325                 330                 335

His Tyr Thr Gln Lys Ser Leu Ser Leu Ser Leu Gly Lys
            340                 345
```

<210> SEQ ID NO 37
<211> LENGTH: 1047
<212> TYPE: DNA

-continued

```
<213> ORGANISM: Artificial sequence
<220> FEATURE:
<223> OTHER INFORMATION: Synthetic polynucleotide

<400> SEQUENCE: 37

gaactgcaac tcgtagaatc tgggggtggc ttggtccagg ccgggggcag tctgcgactt     60

tcctgtgccg catcaggaag gacctccagc atgtatgcga tgggatggtt ccgacaagct    120

ccgggaaatg agcgcgagtt tgttgcggga attggctggg agaataacac gccctattat    180

gctcggtccg tagaggggag gttcactatc agccgagata atgtaaaaaa caccgtattc    240

ctccaaatga atcggttgaa accagaggac gcagcggtct acttttgcgc cgcgcaaatc    300

ggcataagcg gtacattggg ggattactgg ggtcaaggca cacaggtaac cgtctctagt    360

gagtccaaat atggtccccc atgcccacca tgcccagcac ctgagttcct gggggggacca    420

tcagtcttcc tgttcccccc aaaacccaag gacactctca tgatctcccg gacccctgag    480

gtcacgtgcg tggtggtgga cgtgagccag gaagaccccg aggtccagtt caactggtac    540

gtggatggcg tggaggtgca taatgccaag acaaagccgc gggaggagca gttcaacagc    600

acgtaccgtg tggtcagcgt cctcaccgtc ctgcaccagg actggctgaa cggcaaggag    660

tacaagtgca aggtctccaa caaaggcctc ccgtcctcca tcgagaaaac catctccaaa    720

gccaaagggc agccccgaga gccacaggtg tacaccctgc ccccatccca ggaggagatg    780

accaagaacc aggtcagcct gacctgcctg gtcaaaggct tctaccccag cgacatcgcc    840

gtggagtggg agagcaatgg gcagccggag aacaactaca agaccacgcc tcccgtgctg    900

gactccgacg gctccttctt cctctacagc aggctaaccg tggacaagag caggtggcag    960

gaggggaatg tcttctcatg ctccgtgatg catgaggctc tgcacaacca ctacacacag   1020

aagagcctct ccctgtctct gggtaaa                                       1047
```

SINGLE-DOMAIN ANTIBODY TARGETING PD-1, DERIVATIVE THEREOF AND USE THEREOF

TECHNICAL FIELD

The present invention relates to the field of biotechnology. In particular, the invention relates to single-domain antibodies targeting PD-1, derivatives thereof and uses thereof.

REFERENCE TO A "SEQUENCE LISTING,"

The present application contains a Sequence Listing, which is hereby incorporated by reference for all purposes. The accompanying Sequence Listing is submitted in a file entitled "Sequence_Listing_050723-611N01US_ST25.txt," which was created on Jan. 23, 2023, and is approximately 57,344 bytes in size.

BACKGROUND

PD-1 (Programmed cell death protein 1, PD-1) and its ligand PD-L1 are important targets of tumour immunity. PD-1 and PD-L1 are a pair of immunosuppressive molecules which are important components of the immune system to prevent autoimmune overstimulation, and the activation of their pathway has effects of suppressing tumour immune response and inducing apoptosis of tumour-specific T cells, and is closely related to tumour development. The use of monoclonal antibodies to block the PD-1 and PD-L1 pathways for treating tumors exhibits good clinical efficacy and safety. A number of antibody-based drugs have been approved for a variety of malignancies, including melanoma, non-small cell lung cancer and advanced renal cell carcinoma, while many ongoing clinical trials are attempting to develop more new indications.

In addition to activated T cells, NKT cells, B cells and activated monocytes, PD-1 is also highly expressed on the surface of depleted T cells. While its ligand PD-L1 is expressed in organs, such as peripheral microvascular endothelial cells, the heart and lungs, in addition to immune cells, such as B cells, T cells and dendritic cells. And PD-L2 is only expressed on the surface of macrophages and dendritic cells. Notably, the expression of PD-L1 has been widely found in human tumors, including human lung, melanoma, ovarian and colon cancers. In both of in vitro and in vivo assays, blocking the PD-L1/PD-1 pathway significantly increased T-cell proliferation, cytokine secretion and T-cell killing on tumor cells. In animals, blockade of the PD-L1/PD-1 pathway significantly blocked tumor growth. Blocking the PD-1/PD-L1 signalling pathway with a PD-1 antibody significantly enhanced tumor-specific T cell expansion and tumor infiltration. The above results demonstrate the important applications of PD-1/PD-L1 blocking antibodies in tumor therapy.

At present, the FDA has approved three PD-1 antibodies for treating a variety of tumors. All of these approved antibody drugs have achieved good therapeutic results in tumor patients. However, overall clinical response rates are still relatively low, typically around 20%. One strategy to improve the efficacy of PD-1/PD-L1 blocking antibodies is to use bispecific antibodies or multi-targeted fusion proteins that simultaneously block other immune-related or unrelated pathways, including the PD-1/PD-L1 pathway, for achieving synergistic and better therapeutic effects. Bispecific antibodies based on the PD-1/PD-L1 pathway are generally in the form of double-chain antibodies. The molecular weight of bispecific antibodies prepared by this method is generally large, so that it is difficult for the antibody to infiltrate tumor tissue and likely to affect clinical outcomes. Double-chain based bispecific antibodies often suffer from mismatch problems in production, thereby causing significant problems in downstream production and purification. Moreover, current PD-1/PD-L1 monoclonal antibodies suffer from problems, such as high dosing and low overall response rates.

The single domain antibody (sdAb) is a special class of antibodies containing only one antibody heavy chain. Similar to the traditional double-chain antibody, it binds selectively to a specific antigen. Single domain antibodies were first identified in camelids and later in Chondrichthyes, such as nurse sharks. The single domain antibody single heavy chain antibody variable region (VHH) is a single functional domain that binds an intact antigen and is only of 12-15 kDa. The simple structure of VHH offers advantages of high specificity, high affinity, low immunogenicity, good permeability when binding to antigens and the ability to reach more obscure targets that cannot be reached by conventional antibodies when used in the treatment of tumors. In addition, single domain antibodies do not create the mismatch problems associated with the fusion of double chain antibodies, since they have only one chain.

SUMMARY OF THE INVENTION

The purpose of the present invention is to provide a specific single domain antibody targeting PD-1.

Another purpose of the present invention is to provide a specific humanized single domain antibody targeting PD-1.

Still another purpose of the present invention is to provide the use of said single domain antibody or humanized single domain antibody for treating tumors or for preparing drugs for treating tumors.

In the first aspect, the present invention provides a VHH chain of a single domain antibody targeting PD-1, wherein said VHH chain comprises CDR1 shown in SEQ ID NO: 2, CDR2 shown in SEQ ID NO: 3 and CDR3 shown in SEQ ID NO: 4.

In a preferred embodiment, said PD-1 is a human PD-1.

In a preferred embodiment, any one of the above amino acid sequences further comprises a derivative sequence optionally obtained by addition, deletion, modification and/or substitution of at least one (e.g. 1-3, preferably 1-2, more preferably 1) amino acid and capable of retaining binding to PD-1 with high affinity and blocking the binding of PD-L1 to PD-1.

In a preferred embodiment, said VHH chain further comprises the framework regions FR1, FR2, FR3 and FR4, and said FR1, FR2, FR3 and FR4 are shown at positions 1-25, 36-49, 67-98 and 110-120 of the amino acid sequence shown in SEQ ID NO: 1.

In a preferred embodiment, the amino acid sequence of the VHH chain of said single domain antibody targeting PD-1 is shown in SEQ ID NO: 1.

In the second aspect, the invention provides a heavy chain variable region of an antibody targeting PD-1, said heavy chain variable region comprising CDR1 shown in SEQ ID NO: 2, CDR2 shown in SEQ ID NO: 3 and CDR3 shown in SEQ ID NO: 4.

In a preferred embodiment, the amino acid sequence of the heavy chain variable region of said antibody targeting PD-1 is shown in SEQ ID NO: 1.

In the third aspect, the present invention provides a single domain antibody targeting PD-1 having the VHH chain described in the first aspect.

In the fourth aspect, the present invention provides a humanized VHH chain of a single domain antibody targeting PD-1, wherein the framework regions FR1, FR2, FR3 and FR4 are humanized based on the VHH chain described in the first aspect.

In a preferred embodiment, said humanized VHH chains of the single domain antibody targeting PD-1 have the framework regions FR1, FR2, FR3 and FR4 as shown in amino acid positions 1-25, positions 36-49, positions 67-98 and positions 110-120 of the amino acid sequence of SEQ ID NO: 14, or SEQ ID NO: 16, or SEQ ID NO: 18, or SEQ ID NO: 20, or SEQ ID NO: 22, or SEQ ID NO: 24, respectively.

In a preferred embodiment, the amino acid sequence of said humanized VHH chain of the single domain antibody targeting PD-1 is shown in SEQ ID NO: 14, or SEQ ID NO: 16, or SEQ ID NO: 18, or SEQ ID NO: 20, or SEQ ID NO: 22, or SEQ ID NO: 24, respectively.

In the fifth aspect, the present invention provides an antibody targeting PD-1, wherein said antibody comprises one or more VHH chains of a single domain antibody targeting PD-1 as described in the first aspect or a humanized VHH chain of a single domain antibody targeting PD-1 as described in the fourth aspect.

In a preferred embodiment, said antibody targeting PD-1 comprises a monomer, a bivalent antibody, and/or a multivalent antibody.

In the sixth aspect, the present invention provides a bispecific antibody, wherein said bispecific antibody comprises a first antibody and a second antibody, said first antibody comprises a VHH chain of a single domain antibody targeting PD-1 as described in the first aspect, or a heavy chain variable region of an antibody targeting PD-1 as described in the second aspect, or a single domain antibody targeting PD-1 as described in the third aspect, a humanized VHH chain of a single-domain antibody targeting PD-1 as described in the fourth aspect, or an antibody targeting PD-1 as described in the fifth aspect.

In a preferred embodiment, said second antibody may bind the same or a different antigen as the first antibody, or a different epitope of the same antigen as the first antibody.

In a preferred embodiment, said second antibody is a single domain antibody, a single chain antibody or a double chain antibody.

In a preferred embodiment, said bispecific antibody comprises 2-4 single domain antibodies targeting PD-1; preferably, comprising 2 single domain antibodies targeting PD-1; and more preferably, said 2 single domain antibodies targeting PD-1 form a single domain antibody dimer targeting PD-1.

In the seventh aspect, the invention provides a fusion protein, wherein said fusion protein comprises a VHH chain of a single-domain antibody targeting PD-1 as described in the first aspect, a heavy chain variable region of an antibody targeting PD-1 as described in the second aspect, a single-domain antibody targeting PD-1 as described in the third aspect, a humanized VHH chain of a single-domain antibody targeting PD-1 as described in the fourth aspect, or an antibody targeting PD-1 as described in the fifth aspect, an optional linking sequence, and an Fc fragment of an immunoglobulin.

In a preferred embodiment, said immunoglobulin is IgG1, IgG2, IgG3, IgG4; preferably IgG4.

In the eighth aspect, the invention provides a nucleic acid molecule, wherein said nucleic acid molecule encodes a VHH chain of a single-domain antibody targeting PD-1 as described in the first aspect, a heavy chain variable region of an antibody targeting PD-1 as described in the second aspect, a single-domain antibody targeting PD-1 as described in the third aspect, a humanized VHH chain of a single-domain antibody targeting PD-1 as described in the fourth aspect, an antibody targeting PD-1 as described in the fifth aspect, a bispecific antibody as described in the sixth aspect, or a fusion protein as described in the seventh aspect.

In the ninth aspect, the present invention provides an expression vector, wherein said expression vector comprises a nucleic acid molecule as described in the eighth aspect.

In a tenth aspect, the invention provides a host cell, wherein said host cell comprises an expression vector as described in the ninth aspect, or having a nucleic acid molecule as described in the eighth aspect integrated into its genome.

In the eleventh aspect, the present invention provides a method for preparing a VHH chain of a single-domain antibody targeting PD-1 as described in the first aspect, a heavy chain variable region of an antibody targeting PD-1 as described in the second aspect, a single-domain antibody targeting PD-1 as described in the third aspect, a humanized VHH chain of a single-domain antibody targeting PD-1 as described in the fourth aspect, an antibody targeting PD-1 as described in the fifth aspect, a bispecific antibody as described in the sixth aspect, or a fusion protein as described in the seventh aspect, wherein said method comprises steps of:

1) culturing a host cell as described in the tenth aspect under suitable conditions, thereby obtaining a culture containing said VHH chain of a single-domain antibody targeting PD-1, heavy chain variable region of an antibody targeting PD-1, single-domain antibody targeting PD-1, humanized VHH chain of a single-domain antibody targeting PD-1, antibody targeting PD-1, bispecific antibody or fusion protein; and
2) optionally, isolating or recovering said VHH chain of a single-domain antibody targeting PD-1, heavy chain variable region of an antibody targeting PD-1, single-domain antibody targeting PD-1, humanized VHH chain of a single-domain antibody targeting PD-1, antibody targeting PD-1, bispecific antibody or fusion protein from said culture.

In the twelfth aspect, the present invention provides an immunoconjugate, wherein said immunoconjugate comprises:

1) a VHH chain of a single-domain antibody targeting PD-1 as described in the first aspect, a heavy chain variable region of an antibody targeting PD-1 as described in the second aspect, a single-domain antibody targeting PD-1 as described in the third aspect, a humanized VHH chain of a single-domain antibody targeting PD-1 as described in the fourth aspect, an antibody targeting PD-1 as described in the fifth aspect, a bispecific antibody as described in the sixth aspect, or a fusion protein as described in the seventh aspect; and
2) a conjugated moiety selected from a detectable marker, drug, toxin, cytokine, radionuclide, or enzyme.

In a preferred embodiment, said conjugated moiety is a drug or toxin.

In a preferred embodiment, said immunoconjugate is an Antibody-Drug-Couple (ADC).

In a preferred embodiment, said conjugated moiety is a detectable marker.

In a preferred embodiment, said conjugated moiety is selected from a fluorescent or luminescent marker, a radiolabel, an MRI (magnetic resonance imaging) or CT (computed tomography) contrast agent, or an enzyme capable of producing a detectable product, a radionuclide, a biotoxin, a cytokine (e.g. IL-2, etc.), an antibody, an antibody Fc fragment, an antibody scFv fragment, a gold nanoparticle/nanorod, viral particle, liposome, magnetic nanoparticle, prodrug-activating enzyme (e.g., DT-cardiac flavoprotein (DTD) or biphenylyl hydrolase-like protein (BPHL)), chemotherapeutic agent (e.g., cisplatin), or nanoparticle in any form, etc.

In a preferred embodiment, said immunoconjugate comprises: a multivalent (e.g. bivalent) a VHH chain of a single-domain antibody targeting PD-1 as described in claim 1, a heavy chain variable region of an antibody targeting PD-1 as described in claim 2, a single-domain antibody targeting PD-1 as described in claim 3, a humanized VHH chain of a single-domain antibody targeting PD-1 as described in claim 4, an antibody targeting PD-1 as described in claim 5, a bispecific antibody as described in claim 6, or a fusion protein as described in claim 7.

In a preferred embodiment, said "multivalent" means that a plurality of repeat moieties are included in the amino acid sequence of said immunoconjugate.

In the thirteenth aspect, the present invention provides a pharmaceutical composition, wherein said pharmaceutical composition comprises a therapeutically or diagnostically effective amount of a VHH chain of a single-domain antibody targeting PD-1 as described in the first aspect, a heavy chain variable region of an antibody targeting PD-1 as described in the second aspect, a single-domain antibody targeting PD-1 as described in the third aspect, a humanized VHH chain of a single-domain antibody targeting PD-1 as described in the fourth aspect, an antibody targeting PD-1 as described in the fifth aspect, a bispecific antibody as described in the sixth aspect, or a fusion protein as described in the seventh aspect or an immunoconjugate as described in the twelfth aspect, and optionally a pharmaceutically acceptable excipient.

In a preferred embodiment, said pharmaceutical composition is used to treat a tumor, and said tumor is selected from the group consisting of: stomach cancer, liver cancer, leukaemia, kidney tumor, lung cancer, small intestine cancer, bone cancer, prostate cancer, colorectal cancer, breast cancer, colorectal cancer, prostate cancer, cervical cancer, lymphoma, adrenal tumor, or bladder tumor.

In the fourteenth aspect, the invention provides the use of a VHH chain of a single-domain antibody targeting PD-1 as described in the first aspect, a heavy chain variable region of an antibody targeting PD-1 as described in the second aspect, a single-domain antibody targeting PD-1 as described in the third aspect, a humanized VHH chain of a single-domain antibody targeting PD-1 as described in the fourth aspect, an antibody targeting PD-1 as described in the fifth aspect, a bispecific antibody as described in the sixth aspect, or a fusion protein as described in the seventh aspect or an immunoconjugate as described in the twelfth aspect in the preparation of:

1) a reagent for detecting PD-1;
2) a reagent for blocking the binding of PD-1 to PD-L1; or
3) a drug for treating tumors.

In a preferred embodiment, said tumor is selected from the group consisting of: stomach cancer, liver cancer, leukaemia, kidney tumor, lung cancer, small intestine cancer, bone cancer, prostate cancer, colorectal cancer, breast cancer, colorectal cancer, prostate cancer, cervical cancer, lymphoma, adrenal tumor, or bladder tumor.

In the fifteenth aspect, the present invention provides a kit, wherein said kit comprises:

1) a VHH chain of a single-domain antibody targeting PD-1 as described in the first aspect, a heavy chain variable region of an antibody targeting PD-1 as described in the second aspect, a single-domain antibody targeting PD-1 as described in the third aspect, a humanized VHH chain of a single-domain antibody targeting PD-1 as described in the fourth aspect, an antibody targeting PD-1 as described in the fifth aspect, a bispecific antibody as described in the sixth aspect, or a fusion protein as described in the seventh aspect, an immunoconjugate as described in the twelfth aspect, or a pharmaceutical composition as described in the thirteenth aspect;
2) a container; and
3) optionally, an instruction.

In the sixteenth aspect, the invention provides a method for preparing an antibody targeting an immune checkpoint, wherein said method comprises steps of a) immunising an animal using immune cells expressing said immune checkpoint; and
b) obtaining an antibody targeting the immune checkpoint from the immunized animal obtained in step 1).

In a preferred embodiment, said immune cells are primary immune cells.

In a preferred embodiment, said method further comprises a step of activating the immune cells in advance.

In a preferred embodiment, said immune checkpoint includes but not limited to: PD-1, CTLA-4, TIM3, LAG3, KIR, GITR, VISTA, 4-1BB, CD28, OX40, ICOS, etc.

In a preferred embodiment, said immune cells are lymphocytes or phagocytes; preferably, said immune cells are T lymphocytes, B lymphocytes, K lymphocytes, NK lymphocytes, plasma cells, granulocytes, mast cells, antigen presenting cells or cells of the mononuclear phagocyte system (e.g. macrophages); and more preferably T lymphocytes.

In a preferred embodiment, said antibody is a polyclonal antibody, a monoclonal antibody, a monodomain antibody; and preferably a monodomain antibody.

In a preferred embodiment, said animal comprises, but is not limited to, a mouse, a rat, a camel, an alpaca, a llama, a rabbit; and preferably a mouse, an alpaca.

In the seventeenth aspect, the present invention provides a method for detecting PD-1 protein in a sample, wherein said method comprises steps of:

1) contacting a sample to be tested with a VHH chain of a single-domain antibody targeting PD-1 as described in the first aspect, a heavy chain variable region of an antibody targeting PD-1 as described in the second aspect, a single-domain antibody targeting PD-1 as described in the third aspect, a humanized VHH chain of a single-domain antibody targeting PD-1 as described in the fourth aspect, an antibody targeting PD-1 as described in the fifth aspect, a bispecific antibody as described in the sixth aspect, or a fusion protein as described in the seventh aspect, an immunoconjugate as described in the twelfth aspect; and
2) testing the formation of an antigen-antibody complex, the formation of which indicates the presence of PD-1 protein in the sample.

In the eighteenth aspect, the present invention provides a method for treating a disease, wherein said method comprises administering to a subject in need thereof a therapeutically effective amount of a VHH chain of a single-domain antibody targeting PD-1 as described in the first aspect, a heavy chain variable region of an antibody targeting PD-1 as described in the second aspect, a single-domain antibody targeting PD-1 as described in the third aspect, a humanized VHH chain of a single-domain antibody targeting PD-1 as described in the fourth aspect, an antibody targeting PD-1 as described in the fifth aspect, a bispecific antibody as described in the sixth aspect, or a fusion protein as described in the seventh aspect, an immunoconjugate as described in the twelfth aspect, or a pharmaceutical composition as described in the thirteenth aspect.

In a preferred embodiment, said subject comprises a mammal; and preferably a human.

It should be understood that, within the scope of the present invention, each of the above technical features of the present invention and each of the technical features described specifically in the following (e.g. embodiments) can be combined with each other so as to constitute new or preferred technical solutions, which will not be repeated herein for the conciseness of the specification.

MODES FOR CARRYING OUT THE INVENTION

Figure 1:
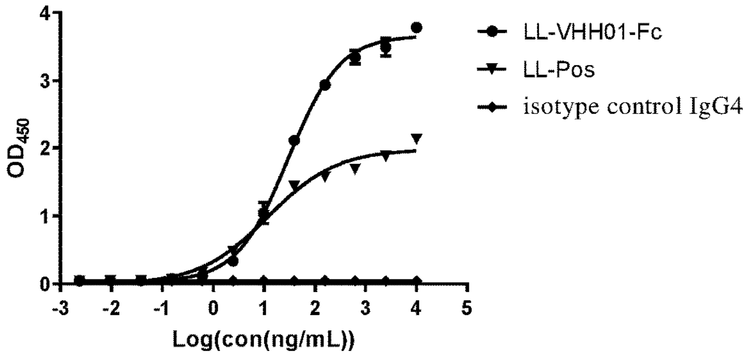
FIG. 1 shows results of affinity assay of VHH-Fc fusion protein, LL-VHH01-Fc binding PD-1 antigen.

The inventors have unexpectedly discovered a class of single domain antibodies targeting PD-1 after extensive and in-depth research. The single domain antibody of the present invention exhibits good binding activity to PD-1 molecules, can block the interaction between PD-1 and PD-L1, and has good anti-tumor activities. Based on this single domain antibody targeting PD-1, the present inventors further developed a series of humanized single domain antibodies, and it was found that these humanized single domain antibodies had similar or better affinity and biological effects than the parent antibody, and had good chemical and serum stability, based on which the present invention was completed.

Definition on Terms

Terms as used herein have same or similar meanings as those routinely understood by a skilled person. For the sake of clarity, some of these terms are defined below.

Antibody

As used herein, the term "antibody" or "immunoglobulin" is a heterotetrameric protein of about 150,000 daltons having the same structural characteristics, consisting of two identical light chains (L) and two identical heavy chains (H). Each light chain is linked to the heavy chains through a covalent disulfide bond, whereas the numbers of disulfide bonds between the heavy chains among different immunoglobulin isoforms are different. Each heavy and light chain also has regularly spaced intrachain disulfide bonds. Each heavy chain has a variable region (VH) at one end, followed by multiple constant regions. Each light chain has a variable region (VL) at one end and a constant region at the other end; the constant region of the light chain corresponds to the first constant region of the heavy chain, and the variable region of the light chain corresponds to the variable region of the heavy chain. Special amino acid residues form the interface between the variable regions of the light and heavy chains.

Single-Domain Antibody

As used herein, "single-domain antibody", "single domain antibody", "nanobody", etc. have the same or similar meanings, and refer to a class of antibody molecules that lack the light chain of the antibody and only have variable regions of the heavy chain. Single-domain antibody is the smallest antigen-binding unit, i.e., the smallest antigen-binding fragment with complete functionality. A single domain antibody (VHH) consisting of only one heavy chain variable region is usually constructed by obtaining an antibody that naturally lacks both the light chain and the constant region 1 (CH1) of the heavy chain, and then cloning the heavy chain variable region of the antibody.

In a specific embodiment, the VHH chain of the single domain antibody targeting PD-1 of the present invention comprises CDR1 shown in SEQ ID NO: 2, CDR2 shown in SEQ ID NO: 3, and CDR3 shown in SEQ ID NO: 4. In a preferred embodiment, the amino acid sequence of the VHH chain of said single domain antibody targeting PD-1 is shown in SEQ ID NO: 1. In said VHH chain, there are also framework regions FR1, FR2, FR3 and FR4, amino acid sequences of which are shown in positions 1-25, 36-49, 67-98 and 110-120 of the amino acid sequence shown in SEQ ID NO: 1.

Based on the VHH chain of the single domain antibody targeting PD-1 of the present invention, the present inventors have also humanized the VHH chain, thereby obtaining a humanized VHH chain of the single domain antibody targeting PD-1. In a specific embodiment, the amino acid sequence of the humanized VHH chain of the present invention is shown in SEQ ID NO: 14, or SEQ ID NO: 16, or SEQ ID NO: 18, or SEQ ID NO: 20, or SEQ ID NO: 22, or SEQ ID NO: 24, respectively. In said humanized VHH chain, framework regions FR1, FR2, FR3 and FR4 are also included, amino acid sequences of which are shown in positions 1-25, 36-49, 67-98 and 110-120 positions of the amino acid sequences shown in SEQ ID NO: 14, or SEQ ID NO: 16, or SEQ ID NO: 18, or SEQ ID NO: 20, or SEQ ID NO: 22, or SEQ ID NO: 24, respectively.

Based on the VHH chain of the single domain antibody targeting PD-1 of the present invention or the humanized VHH chain, the present invention also provides an antibody targeting PD-1 comprising one or more of said VHH chains of the single domain antibody targeting PD-1 or the humanized VHH chain of the single domain antibody targeting PD-1. The present invention also provides a bispecific antibody, said bispecific antibody comprises the first antibody and the second antibody, and the first antibody may be a VHH chain of a single domain antibody targeting PD-1 of the present invention, or a humanized VHH chain. A skilled person may select the second antibody of said bispecific antibody as desired. For example, said second antibody may bind the same or a different antigen from the first antibody; and if the second antibody binds the same antigen as the first antibody, it preferably binds to a different epitope. In a specific embodiment, the second antibody may be a single domain antibody, a single chain antibody or a double chain antibody.

A skilled person can also prepare a fusion protein from a VHH chain of the single domain antibody targeting PD-1 of the present invention or a humanized VHH chain, for example, prepare a fusion protein further comprising the Fc fragment of an immunoglobulin. The fusion protein thus obtained not only possesses biological activities of the VHH chain of a single-domain antibody itself, but also possesses other properties conferred by the Fc fragment of the immunoglobulin, such as prolonged plasma half-life, reduced immunogenicity, improved stability, and the like. In a specific embodiment, said fusion protein comprises a VHH chain of a single domain antibody targeting PD-1 of the invention or a humanized VHH chain, an optional linker sequence, and an Fc fragment of an immunoglobulin. In a specific embodiment, said immunoglobulin is IgG1, IgG2, IgG3, IgG4; and preferably IgG4.

The present invention includes not only complete antibodies, but also fragments, derivatives and analogs of said antibodies. As used herein, the terms "fragment", "derivative" and "analog" refer to a polypeptide which retains essentially the same biological function or activity as the antibody of the present invention. The polypeptide fragment, derivatives or analogs of the present invention may be (i) a polypeptide having one or more conserved or non-conserved amino acid residues (preferably conserved amino acid residues) being replaced, and such replaced amino acid residues may or may not be encoded by the genetic code, or (ii) a polypeptide having substituents in one or more amino acid residues, or (iii) a polypeptide formed by fusing a mature polypeptide with another compound (e.g., a compound that extends the half-life of the polypeptide, e.g., polyethylene glycol), or (iv) a polypeptide formed by fusion of additional amino acid sequences to this polypeptide sequence (e.g., a leading sequence or a secretory sequence or a sequence used to purify this polypeptide or a proteogenic sequence, or a fusion protein formed with a 6His tag). According to the teachings herein, these fragments, derivatives and analogs fall within the scope of what is known to a skilled person.

The antibody of the present invention refers to a polypeptide having PD-1 protein-binding activity and comprising the CDR regions described above. The term also includes variant forms of a polypeptide having the same function as the antibody of the present invention and comprising the CDR regions described above. These variant forms include, but are not limited to, deletions, insertions and/or substitutions of one or more (typically 1-50, preferably 1-30, more preferably 1-20, and the most preferably 1-10) amino acids, and the addition of one or more (typically up to 20, preferably up to 10, and more preferably up to 5) amino acids to the C-terminus and/or N-terminus. For example, substitutions with amino acids of similar or analogous properties typically do not alter the function of proteins in the art. For another example, the addition of one or several amino acids to the C-terminus and/or the N-terminus does not usually alter the function of the protein either. The term also includes active fragments and active derivatives of the antibody of the present invention. Variant forms of the polypeptide include: homologous sequences, conserved variants, allelic variants, natural mutants, induced mutants, proteins encoded by DNA capable of hybridizing to the DNA encoding the antibody of the present invention under conditions of high or low stringency, and polypeptides or proteins obtained by utilizing antisera against the antibody of the present invention.

In addition to a nearly full-length polypeptide, the present invention includes fragments of single domain antibodies of the present invention. Typically, the fragment has at least about 50 contiguous amino acids, preferably at least about 50 contiguous amino acids, more preferably at least about 80 contiguous amino acids, and the most preferably at least about 100 contiguous amino acids of the antibody of the present invention.

In the present invention, "the conservative variant of the antibody according to the present invention" includes polypeptides which, compared with the amino acid sequence of the antibody according to the present invention, are formed by replacing at most 10, preferably at most 8, more preferably at most 5, most preferably at most 3 amino acid with amino acids having similar properties. These conservative variant may be preferably generated through amino acid replacements as shown in, for example the following table.

| Initial residue | Representative residues for replacement | Preferred residues for replacement |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides a polynucleotide encoding the above antibody, or a fragment or fusion protein thereof. The polynucleotides of the present invention may be in the form of DNA or RNA. The form of DNA includes cDNA, genomic DNA or synthetic DNA. The DNA may be single-stranded or double-stranded. The DNA may be a coding or non-coding chain. A polynucleotide encoding a mature polypeptide of the invention includes: a coding sequence encoding only the mature polypeptide; a coding sequence of the mature polypeptide and various additional coding sequences; a coding sequence (and optionally additional coding sequences) of the mature polypeptide and non-coding sequences.

The term "polynucleotide encoding a polypeptide" may include a polynucleotide encoding such polypeptide, and may further include a polynucleotide with additional coding and/or non-coding sequences. The present invention also relates to a polynucleotides which hybridises to the sequence described above and which has at least 50%, preferably at least 70%, more preferably at least 80% identity with that sequence. In particular, the present invention relates to polynucleotides which can hybridise to the polynucleotides described herein under stringent conditions. In the present invention, "stringent condition" means: (1) hybridisation and elution at lower ionic strengths and higher temperatures, e.g., 0.2×SSC, 0.1% SDS, 60° C.; or (2) hybridisation with a denaturant, e.g., 50% (v/v) formamide, 0.1% calf serum/0.1% Ficoll, 42° C., etc.; or (3) hybridisation occurs only when the identity between the two sequences is at least 90%, preferably more than 95%. Moreover, the polypeptide encoded by a hybridisable polynucleotide has the same biological function and activity as the mature polypeptide.

The full-length nucleotide sequences of the antibodies of the present invention, or fragments thereof, can usually be obtained by PCR amplification, recombinant methods or synthetic methods. One possible method is to synthesise a sequence by synthetic methods, especially when the fragment is relatively short in length. Typically, fragments with long sequences can be obtained by first synthesising a plurality of small fragments and then ligating them together. In addition, the coding sequence of the heavy chain can be fused together with an expression tag (e.g. 6His) to form a fusion protein. Once the sequence has been obtained, recombinant methods can be used to obtain the sequence in large quantities. This is typically performed by cloning the sequence into a vector, transferring the vector into a cell, and then isolating the sequence from the proliferated host cell by conventional methods. The biomolecules (nucleic acids, proteins, and the like) to which the present invention relates, include biomolecules in isolated form.

Nowadiay, it is possible to obtain a DNA sequence encoding a protein of the invention (or a fragment or derivative thereof) entirely by chemical synthesis. Such DNA sequence can then be introduced into various existing DNA molecules (or vectors) and cells known in the art. In addition, mutations may be introduced into the protein sequence of the present invention by chemical synthesis.

The present invention also relates to vectors comprising the appropriate DNA sequences as described above, as well as appropriate promoters or control sequences. These vectors can be used to transform appropriate host cells to enable them to express proteins. The host cell may be a prokaryotic cell, such as a bacterial cell; or a lower eukaryotic cell, such as a yeast cell; or a higher eukaryotic cell, such as a mammalian cell. Representative examples include: bacterial cells, such as *Escherichia coli, Streptomyces* spp; *Salmonella typhimurium*; fungal cells, such as yeast; insect cells, such as *Drosophila* S2 or Sf9; and animal cells, such as CHO, COS7, 293 cells.

The transformation of host cells with a recombinant DNA can be performed by conventional techniques well known to a skilled person. When the host is a prokaryote, such as *E. coli*, competent cells capable of taking up DNAs can be harvested after an exponential growth period and treated with $CaCl_2$), using steps well known in the art. Another method is to use $MgCl_2$. The transformation can also be performed by electroporation if desired. When the host is an eukaryotic, following methods of DNA transfection are available: calcium phosphate co-precipitation; conventional mechanical methods, such as microinjection, electroporation, and liposome packaging.

The obtained transformants can be cultured by conventional methods to express the polypeptides encoded by the genes of the present invention. Depending on the host cells used, the medium used in the culture may be selected from a variety of conventional media. The culture is carried out under conditions suitable for the growth of the host cells. After the host cells have grown to an appropriate cell density, the selected promoter is induced by a suitable method (e.g., temperature shift or chemical induction) and the cells are cultured for an additional period of time.

In the above methods, the recombinant polypeptides may be expressed inside the cell, or on the cell membrane, or secreted outside the cell. If desired, the recombinant proteins can be isolated and purified by various separation methods using their physical, chemical and other properties. These methods are well known to a skilled person. Examples of these methods include, but are not limited to: conventional renaturation treatment, treatment with protein precipitants (salting-out methods), centrifugation, osmotic bacterial breakage, ultra-treatment, ultra-centrifugation, molecular sieve chromatography (gel filtration), adsorption chromatography, ion-exchange chromatography, high-performance liquid chromatography (HPLC), and a variety of other liquid chromatography techniques, and combinations of these methods.

The antibodies of the present invention may be used alone or in combination with or conjugated with a detectable marker (for diagnostic purposes), a therapeutic agent, a PK (protein kinase) modifying portion, or any combination thereof. Detectable markers for diagnostic purposes include, but are not limited to: fluorescent or luminescent markers, radiolabelled markers, MRI (Magnetic Resonance Imaging) or CT (Computerised Tomography) contrast agents, or enzymes capable of producing detectable products.

Therapeutic agents that may be bound or conjugated with antibodies of the present invention include, but are not limited to: 1. radionuclides; 2. biotoxins; 3. cytokines, such as IL-2, etc.; 4. gold nanoparticles/nanorods; 5. viral particles; 6. liposomes; 7. magnetic nanoparticles; 8. drug-activating enzymes (e.g., DT-cardiac dystrophinase (DTD) or biphenyl hydrolase-like protein (BPHL)); 9. therapeutic agents (e.g., cisplatin) or any form of nanoparticles, etc.

Immune Checkpoint

As used herein, immune checkpoint or immune checkpoint molecule has the same meaning as conventionally understood by a skilled person. It refers to a series of molecules expressed on immune cells that can regulate the degree of immune activation, and play an important role in preventing autoimmunity (abnormalities in immune function that result in attacks on normal cells) from occurring. Therefore, one of the important functions of "immune checkpoint molecules" is to keep the activation of the immune system within a normal range in order to prevent over-activation of the immune system.

Abnormal expression and function of immune checkpoint molecules is one of the important reasons for the occurrence of many diseases. For example, if immune checkpoint molecules are over-expressed or the function of immune checkpoint molecules are too strong, the immune function will be suppressed, the body's immunity will be low, and a person is susceptible to tumors and other diseases. On the contrary, if such immune-suppressing function of the immune checkpoint molecules is poor, the body's immune function will also be abnormal. Tumor cells will express some substances to activate the immune checkpoints, and once the latter are activated, the antigen cannot be presented to the T cells, thereby blocking the process of presenting the antigen in the tumor immune loop, thus suppressing the immune function of T cells, allowing the tumor cells to escape from immune surveillance and thus survive.

Commonly used immune checkpoints include CTLA-4 (cytotoxic T lymphocyte-associated antigen-4), PD-1, TIM3, LAG3, KIR, GITR, VISTA, and 4-1BB.

Immune Cells

As used herein, immune cells and immune effector cells have the same meaning as conventionally understood by a skilled person, which refer to cells that are involved in or associated with an immune response, including lymphocytes and phagocytes. In a specific embodiment, said immune cells refer to lymphocytes that recognise antigens and thereby generate a specific immune response. Said lymphocytes are mainly T lymphocytes, B lymphocytes, K lymphocytes and NK lymphocytes. In addition to lymphocytes, cells involved in the immune response are plasma cells, granulocytes, mast cells, antigen-presenting cells and cells of the mononuclear phagocyte system (e.g. macrophages).

Immunogonjugate

The present invention also provides an immunoconjugate comprising a VHH chain of a single domain antibody targeting PD-1 of the present invention, a humanised VHH chain and the like, and a conjugated moiety. In a specific embodiment, said conjugated moiety may be a detectable marker, drug, toxin, cytokine, radionuclide, or enzyme, etc., for diagnostic, detection or therapeutic purposes, and the like.

In a preferred embodiment, said immunoconjugate is an Antibody-Drug-Conjugate (ADC).

Pharmaceutical Composition

The present invention also provides a composition. Preferably, said composition is a pharmaceutical composition comprising an antibody as described above or an active fragment thereof or a fusion protein thereof, and a pharmaceutically acceptable carrier. Typically, these substances may be formulated in a non-toxic, inert, and pharmaceutically acceptable aqueous carrier medium, wherein the pH is typically about 5-8, and preferably about 6-8, although the pH may vary depending on the nature of the substance to be formulated and the condition to be treated. A formulated pharmaceutical composition can be administered by conventional routes, including (but not limited to): intratumoral, intraperitoneal, intravenous, or topical administration.

The pharmaceutical compositions of the present invention can be used to bind PD-1 protein directly, thereby blocking the interaction of PD-1 and PD-L1. Therefore, the pharmaceutical compositions of the present invention can be used to treat tumors. In a preferred embodiment, said tumor is selected from the following group: gastric cancer, liver cancer, leukaemia, kidney tumor, lung cancer, small intestine cancer, bone cancer, prostate cancer, colorectal cancer, breast cancer, colorectal cancer, prostate cancer, cervical cancer, lymphoma, adrenal gland tumor, or bladder tumor. In addition, the pharmaceutical compositions of the present invention may be used in combination with other therapeutic agents.

The pharmaceutical composition of the present invention comprises a safe and effective amount (e.g., 0.001-99 wt %, preferably 0.01-90 wt %, and more preferably 0.1-80 wt %) of the above described single domain antibody of the present invention (or a conjugate thereof) as well as a pharmaceutically acceptable carrier or excipient. Such carriers include (but are not limited to): saline, buffer, glucose, water, glycerol, ethanol, and combinations thereof. The pharmaceutical formulation should be compatible with the mode of administration. The pharmaceutical composition of the present invention may be prepared into the form of an injection, e.g. prepared by conventional methods using saline or an aqueous solution containing glucose and other excipients. A pharmaceutical composition, such as injection and solution is preferably manufactured under sterile conditions.

The active ingredient is administered in a therapeutically effective amount, e.g., about 10 mg/kg body weight—about 50 mg/kg body weight per day. When using the pharmaceutical composition, a safe and effective amount of the immunoconjugate is administered to a mammal, wherein the safe and effective amount is usually at least about 10 μg/kg body weight and in most cases not more than about 50 mg/kg body weight, and preferably the dose is about 10 μg/kg body weight—about 10 mg/kg body weight. Of course, the route of administration, the patient's health status and other factors should also be taken into account for the exact dose, which are within the skill of the skilled practitioner.

Detection Method

The present invention also relates to a method for detecting PD-1 protein. Steps of the method are substantially as follows: contacting the sample to be tested with a VHH chain of a single domain antibody targeting PD-1 of the present invention, or a humanised VHH chain, an antibody, a fusion protein or an immunoconjugate, etc.; and subsequently detecting the formation of an antigen-antibody complex, the formation of which would indicate the presence of PD-1 protein in the sample.

Kit

The present invention also provides a kit comprising a VHH chain of a single domain antibody targeting PD-1 of the present invention, or a humanised VHH chain, an antibody, a fusion protein or an immunoconjugate, etc. In a specific embodiment, said kit further comprises a container, instruction, buffer, and the like.

Method for Preparing an Antibody Targeting an Immune Checkpoint

During the course of research, the present inventors found that the activities of PD-1 single domain antibodies obtained by directly immunising animals using PD-1 protein were poor. However, when the present inventors used T cells for immunisation, PD-1 single domain antibodies with good activities were obtained.

Based on the above findings, the present invention also provides a particular immunisation method, which will enable the preparation of antibodies targeting an immune checkpoint. Said method comprises immunising an animal using immune cells expressing an immune checkpoint. In a preferred embodiment, an animal can be immunised using immune cells expressing the immune checkpoint after said immune cells are activated. Methods or technical means for activating immune cells are well known to a skilled person.

In the method of the present invention for preparing an antibody targeting an immune checkpoint, the used immune cells are preferably primary immune cells. In the method of the present invention, the immunised animals include, but are not limited to, mice, llamas, alpacas, rats, rabbits; preferably mice, alpacas. The antibody obtained by the method of the present invention may be a polyclonal antibody, a monoclonal antibody, a single domain antibody.

Advantages of the Invention 1. the single domain antibody targeting PD-1 of the present invention exhibits good binding affinity to PD-1, and thus is able to effectively block PD-1 and PD-L1 binding;
2. the humanised single domain antibody of the present invention is able to retain good binding affinity to PD-1 and exhibits similar, or even better, biological effects than the parent antibody at the in vitro cellular level;
3. the humanised single domain antibody of the present invention has excellent chemical and serum stability; and
4. the single domain antibody targeting PD-1 and the humanised single domain antibody of the present invention have wide biological application value and clinical application value, thereby laying a new material foundation for the development of therapeutic or diagnostic drugs targeting PD-1.

The present invention is further described below in connection with specific embodiments. It should be understood that these embodiments are used only to illustrate the invention and are not intended to limit the scope of the invention. Experimental methods for which specific conditions are not indicated in the following embodiments are generally in accordance with conventional conditions, such as those described in Sambrook et al, Molecular Cloning: a Laboratory Manual (New York: Cold Spring Harbor Laboratory Press, 1989), or in accordance with conditions recommended by the manufacturer. Unless otherwise indicated, percentages and parts are weight percentages and weight parts.

Example 1: Construction of Phage Display Immune Library 1.1 Immunisation of Animals Frozen human peripheral blood mononuclear cells (purchased from Myotonics) were recovered and the concentration was adjusted to $2*10^6$/ml. And then micro magnetic beads (Thermo Fisher Scientific) loaded with CD3 and CD28 antibodies were added according to the recommended ratio to activate T cells in the PBMCs. After the T cells were activated, the magnetic beads were removed using a magnetic rack; the cells were then collected by centrifugation at 1600 rpm for 5 min; and the cells were frozen in a freezing medium. The freezing medium was RPMI-1640:FBS:DMSO=4:5:1. Temporarily, the frozen cells were stored in liquid nitrogen.

An adult healthy alpaca was selected. The frozen T cells were firstly resuscitated and then the cells were washed once using 1*PBS. The cells were resuspended in a buffer, and then used in the subcutaneous immunisation of the alpaca. The alpaca was then immunised for five times using the same method.

1.2 Construction of Phage Library

After the immunisation was completed, 50 mL each of peripheral blood was collected from alpacas after the 4th and 5th immunisation, and mixed to isolate peripheral blood mononuclear cells (PBMCs). Total RNAs were further extracted using RNAiso Plus reagent (Takara, Cat no. 9109). The extracted total RNAs were reverse-transcribed using PrimeScript™ II 1st Strand cDNA Synthesis Kit (Takara, Cat no. 6210A) according to the instructions provided with the kit. DNA fragments of the heavy chain variable region of alpaca were amplified using nested PCR. A total of two rounds of nested PCR were performed.

The vector (pComb3XSS) and the PCR-amplified target fragments were digested separately using SfiI overnight at 50° C., and the target fragments were recovered. The digested PCR products were ligated with the vector at a molar ratio of vector:PCR product=1:3. The vector ligated with a VHH was introduced into competence cells using an electrotransformation method to construct a phage display library of the heavy chain single domain antibody. The cells were plated after the electrotransformation. For testing the insertion rate of the library, 48 clones on the plate were randomly selected for colony PCR. Results showed that the insertion rate reached 100%. The cells were gradient-diluted and plated, and the size of the library was calculated to be $1.0\times10^9$. The bacteria library was innoculated into 2× 300 mL 2YT+A+G (Amp: 100 μg/ml, Glu: 1%) medium with an initial $OD_{600}$=0.1-0.2, and incubated at 37° C. and 230 rpm until $OD_{600}$=0.8 or higher. Phage libraries were prepared by adding helper phage M13KO7, (helper phage:bacteria=20:1) according to the $OD_{600}$ value. The phage library was gradient-diluted and plated, and the phage library titer was measured to be $5.76\times10^{13}$ cfu/mL by counting the number of clones.

Example 2: Screening of Anti-Human PD-1 Single Domain Antibody

The constructed immune library of alpaca was screened for affinity by solid phase screening to obtain a specific phage library.

2.1 Affinity Panning 2.1.1 Panning 1) the target antigen was diluted with a carbonate buffer at pH 9.6 to a final concentration of 5 μg/mL, and then added to the wells of a microplate reader at 100 μL/well, and coated at 4° C. overnight;
2) the coating solution was discarded and washed for 3 times with PBS. Afterwards, 300 μL of 3% BSA-PBS blocking solution was added to each well and blocked at 37° C. for 1 hour;
3) afterwards, the blocking solution was discarded and washed for 3 times with PBS. 100 μL of phage library was added and incubated at 37° C. for 1 hour;
4) unbound phage was aspirated and the plate was washed for 6 times with PBST and 2 times with PBS;
5) 100 μL of Gly-HCl eluate was added to each well and incubated at 37° C. for 8 min;
6) the eluate was transferred to a 1.5 mL sterile centrifuge tube and quickly neutralised with 15 μL of Tris-HCl neutralisation buffer;
7) 10 μL of the neutralised solution was taken and subjected to a gradient dilution, the phage titer was determined and the panning recovery rate was calculated. The remaining eluate was mixed, amplified and purified for the next round of affinity panning. The panning conditions were changed, and the panning conditions for each round are shown in Table 1.

TABLE 1

| Affinity panning condition | | | | | | |
|---|---|---|---|---|---|---|
| Round | Antigen Coating Concentration (μg/mL) | blocking solution | Amount of added library (cfu) | Binding time (h) | PBST Concentration | Number of washing with PBST |
| 1 | 5 | BSA-PBS | $2\times10^{11}$ | 1 | 0.1% | 6 |
| 2 | 5 | OVA-PBS | $1\times10^{11}$ | 0.75 | 0.25% | 8 |

2.1.2 Library Amplification

After panning, it was necessary to amplify the library with main steps as follows:

1) the panned eluate was mixed with 5 mL of *E. coli* TG1 culture in the pre-logarithmic growth phase, stood for 30 min at 37° C., and then incubated for 30 min with 220 r/min oscillation;
2) centrifuged at 1000 g for 15 min to remove the supernatant, resuspended in 500 μL of 2×YT and plated on a 200 mm 2×YT-GA plate;

3) *E. coli* cells were scraped into 10 ml of 2×YT liquid medium, 500 μl of suspension was taken and added into 50 ml of 2×YT liquid medium, shaken at 37° C. for 30 min; M13KO7 helper phage was added according to the ratio of cell:phage=1:20, stood at 37° C. for 30 min, and then incubated for 30 min by shaking at 220 r/min;

4) the culture was dispensed into centrifuge tubes at 25° C., 5000 r/min for 10 min, and the cell precipitate was resuspended in 50 mL of 2×YT-AK Liquid Medium, and incubated overnight at 30° C., 230 r/min with shaking;

5) the overnight culture was centrifuged at 4° C., 10000 r/min for 20 mins, the supernatant was transferred to a new centrifuge tube, ⅕ volume of PEG-NaCl was added, mixed well and placed at 4° C. for more than 2 h;

6) the mixture was centrifuged at 4° C., 10000 r/min for 20 mins, the supernatant was removed, and the precipitate was resuspended in 1 mL of PBS, and ⅕ volume of PEG/NaCl was added, mixed well and placed at 4° C. for more than 1 h;

7) the mixture was centrifuged at 4° C., 12000 r/min, 2 min, the supernatant was removed, and the precipitate was resuspended in 200 μL of PBS, which was the amplification product, determined for the titer, and used for the next round of panning or analysis.

2.1.3 Phage Rescue 1) 96 monoclones were randomly picked from the plate of the second round of panned eluent titer with a sterilised toothpick, inoculated into 1 mL of 2×YT-A, and incubated for 8 h at 37° C. with 220 r/min oscillation;

2) 200 μL of the above culture was taken, M13KO7 phage was added at a ratio of cell:phage=1:20, 37° C., and stood for 15 min;

3) the culture was shaken at 220 r/min for 45 min;

4) 800 μL of 2×YT-AK was added, incubated overnight at 30° C. with vigorous shaking;

5) centrifuged on the next day at 12000 rpm for 2 min;

6) the supernatant was taken and used for monoclonal ELISA identification.

2.1.4 Identification of Positive Phage Clones

1) PD-1 antigen was diluted in carbonate buffer at pH 9.6 to a final concentration of 2 μg/mL, added to wells of a micro-plate reader at 100 μL/well, and coated at 4° C. overnight;

2) the coating solution was discarded and washed with PBST for 3 times;

3) 300 μL of 5% skimmed milk was added into each well which was blocked at 37° C. for 1 h;

4) each well was washed for 3 times with PBST, and 50 μL of phage culture supernatant and 50 μL of 5% skimmed milk were added into each well and incubated for 1 h at 37° C.;

5) each well was washed for 5 times, and then horseradish peroxidase-labelled anti-M13 antibody (diluted 1:10,000 with 5% skimmed milk) was added at 100 μl/well, and incubated for 1 h at 37° C.;

6) the plate was washed for 6 times with PBST. TMB colour development solution was added for the development at 100 μL/well, 37° C., 7 min;

7) a quenching solution was added to quench the reaction at 50 μL/well, and the optical density was measured at 450 nm.

2.2 Sequencing of positive clones

Three positive clones were detected. The three positive clones were sent to Suzhou Hongxun Biotechnology Co. for sequencing. One of the clones was sequenced successfully. The sequencing results were analysed to obtain the VHH region of the anti-PD-1 antibody, which was named as LL-VHH01. The CDR region of LL-VHH01 was analysed using Kabat nomenclature, and the corresponding sequences of the CDR regions were obtained. The amino acid sequences of the 0 full-length and the CDR region of LL-VHH01 are shown in Table 2, and the nucleic acid sequences are shown in Table 3.

TABLE 2

Amino acid sequence of VHH and corresponding amino acid sequence of CDR

| Name | Amino acid sequence | CDR1 | CDR2 | CDR3 |
|---|---|---|---|---|
| LL-VHH01 | QLQLVESGGGLVQAGGSLRLSCAASGRTSSMYAMGWFRQSPGNEREFVAGIGWENNTPYYARSVEGRFTISRDNVKNTVFLQMNRLKPEDAAVYFCAAQIGISGTLGDYWGQGTQVTVSS (SEQ ID NO: 1) | GRTSSMYAMG (SEQ ID NO: 2) | GIGWENNTPYYARSVEG (SEQ ID NO: 3) | QIGISGTLGDY (SEQ ID NO: 4) |

The amino acid sequence of LL-VHH01 is SEQ ID NO: 1, the sequence of CDR1 is SEQ ID NO: 2, the sequence of CDR2 is SEQ ID NO: 3, and the sequence of CDR3 is SEQ ID NO: 4.

TABLE 3

Nucleic acid sequence of LL-VHH01 and corresponding nucleic acid sequence of CDR

| Name | Nucleic acid sequence | CDR1 | CDR2 | CDR3 |
|---|---|---|---|---|
| LL-VHH01 | CAGTTGCAGCTCGTGGAGTCGGGAGGAGGGCTGGTGCAGGCTGGGGGCTCTCTGAGACTCTCCTGTGCAGCCTCTGGACGCACCTCCAGTATGTATGCCATGGGCTGGTTCCGCCAGTCTCCAGGGAACGAGCGCGAGTTTGTAGCGGGGATTGGCTGGGAGAATAATACCCCAT | GGACGCACCTCCAGTATGTATGCCATGGGC (SEQ ID NO: | GGGATTGGCTGGGAGAATAATACCCCATACTATGCACGCTCCGTGGAGG | CAAATCGGAATATCCGGTACATTGGGGGACTAC (SEQ ID NO: 8) |

TABLE 3-continued

| Nucleic acid sequence of LL-VHH01 and corresponding nucleic acid sequence of CDR | | | | |
|---|---|---|---|---|
| Name | Nucleic acid sequence | CDR1 | CDR2 | CDR3 |
| | ACTATGCACGCTCCGTGGAGGGCCG ATTCACCATCTCCAGAGACAACGTC AAGAACACGGTCTTTCTACAAATGA ACAGACTGAAACCTGAGGACGCGGC CGTTTATTTTTGTGCAGCCCAAATC GGAATATCCGGTACATTGGGGGACT ACTGGGGCCAGGGGACCCAGGTCAC CGTCTCCTCA (SEQ ID NO: 5) | 6) | GC (SEQ ID NO: 7) | |

Example 3: Preparation of PD-1 Single Domain Antibody VHH-Fc Fusion Protein

The amino acid sequence of the constant region of human immunoglobulin gamma4 (IgG4) was obtained from the database Uniprot (P01861).

(SEQ ID NO: 9)
ESKYGPPCPPCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGK

The amino acid sequence of PD-1 single domain antibody VHH and the amino acid sequence of hIgG4-Fc were ligated to obtain the PD-1 VHH-Fc fusion protein, named as: LL-VHH01-Fc. The gene sequence of anti-human PD-1 single domain antibody VHH-Fc fusion protein LL-VHH01-Fc was obtained by gene synthesis.

The gene of PD-1 VHH-Fc fusion protein was then cloned into the expression vector pCDNA4 (Invitrogen, Cat V86220). The PD-1 single domain antibody VHH-Fc fusion protein LL-VHH01-Fc was expressed by using transient transfection of HEK293 suspension cells. Upon the completion of expression, the supernatant was collected and purified using a Protein A affinity chromatography column to ultimately obtain the purified Fc fusion protein LL-VHH01-Fc of the PD-1 single domain antibody.

LL-VHH01-Fc
Gene sequence is:
SEQ ID NO: 10
CAGTTGCAGCTCGTGGAGTCGGGAGGAGGGCTGGTGCAGGCTGGGGGCTC
TCTGAGACTCTCCTGTGCAGCCTCTGGACGCACCTCCAGTATGTATGCCA
TGGGCTGGTTCCGCCAGTCTCCAGGGAACGAGCGCGAGTTTGTAGCGGGG
ATTGGCTGGGAGAATAATACCCCATACTATGCACGCTCCGTGGAGGGCCG
ATTCACCATCTCCAGAGACAACGTCAAGAACACGGTCTTTCTACAAATGA
ACAGACTGAAACCTGAGGACGCGGCCGTTTATTTTTGTGCAGCCCAAATC
GGAATATCCGGTACATTGGGGGACTACTGGGGCCAGGGGACCCAGGTCAC
CGTCTCCTCAGAGTCCAAATATGGTCCCCCATGCCCACCATGCCCAGCAC
CTGAGTTCCTGGGGGGACCATCAGTCTTCCTGTTCCCCCCAAAACCCAAG
GACACTCTCATGATCTCCCGGACCCCTGAGGTCACGTGCGTGGTGGTGGA -continued CGTGAGCCAGGAAGACCCCGAGGTCCAGTTCAACTGGTACGTGGATGGCG
TGGAGGTGCATAATGCCAAGACAAAGCCGCGGGAGGAGCAGTTCAACAGC
ACGTACCGTGTGGTCAGCGTCCTCACCGTCCTGCACCAGGACTGGCTGAA
CGGCAAGGAGTACAAGTGCAAGGTCTCCAACAAAGGCCTCCCGTCCTCCA
TCGAGAAAACCATCTCCAAAGCCAAAGGGCAGCCCCGAGAGCCACAGGTG
TACACCCTGCCCCCATCCCAGGAGGAGATGACCAAGAACCAGGTCAGCCT
GACCTGCCTGGTCAAAGGCTTCTACCCCAGCGACATCGCCGTGGAGTGGG
AGAGCAATGGGCAGCCGGAGAACAACTACAAGACCACGCCTCCCGTGCTG
GACTCCGACGGCTCCTTCTTCCTCTACAGCAGGCTAACCGTGGACAAGAG
CAGGTGGCAGGAGGGGAATGTCTTCTCATGCTCCGTGATGCATGAGGCTC
TGCACAACCACTACACACAGAAGAGCCTCTCCCTGTCTCTGGGTAAA.

Amino acid sequence is:
SEQ ID NO: 11
QLQLVESGGGLVQAGGSLRLSCAASGRTSSMYAMGWFRQSPGNEREFVAG
IGWENNTPYYARSVEGRFTISRDNVKNTVFLQMNRLKPEDAAVYFCAAQI
GISGTLGDYWGQGTQVTVSSESKYGPPCPPCPAPEFLGGPSVFLFPPKPK
DTLMISRTPEVTCVVVDVSQEDPEVQFNWYVDGVEVHNAKTKPREEQFNS
TYRVVSVLTVLHQDWLNGKEYKCKVSNKGLPSSIEKTISKAKGQPREPQV
YTLPPSQEEMTKNQVSLTCLVKGFYPSDIAVEWESNGQPENNYKTTPPVL
DSDGSFFLYSRLTVDKSRWQEGNVFSCSVMHEALHNHYTQKSLSLSLGK.

Example 4: Preparation of PD-1 Positive Control Antibody

The amino acid sequence of Pembrolizumab, an anti-PD-1 antibody from Merck Sharp & Dohme (MSD), was obtained from WO2008156712A1, in which the amino acid sequence of the heavy chain is SEQ ID NO: 12.

QVQLVQSGVEVKKPGASVKVSCKASGYTFTNYYMYWVRQAPGQGLEWMGG
INPSNGGTNFNEKFKNRVTLTTDSSTTTAYMELKSLQFDDTAVYYCARRD
YRFDMGFDYWGQGTTVTVSSASTKGPSVFPLAPCSRSTSESTAALGCLVK
DYFPEPVTVSWNSGALTSGVHTFPAVLQSSGLYSLSSVVTVPSSSLGTKT
YTCNVDHKPSNTKVDKRVESKYGPPCPPCPAPEFLGGPSVFLFPPKPKDT
LMISRTPEVTCVVVDVSQEDPEVQFNWYVDGVEVHNAKTKPREEQFNSTY

-continued

```
RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK.
```

the amino acid sequence of the light chain is SEQ ID NO: 13.

```
EIVLTQSPATLSLSPGERATLSCRASKGVSTSGYSYLHWYQQKPGQAPRL

LIYLASYLESGVPARFSGSGSGTDFTLTISSLEPEDFAVYYCQHSRDLPL

TFGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

Analogues of Pembrolizumab antibody were also expressed and purified according to the expression and purification method of antibody in the application. The anti-PD-1 antibody analogue from MSD was obtained and renamed as LL-Pos.

Example 5: Detection of Binding Ability of PD-1 Single Domain Antibody VHH-Fc Fusion Protein to PD-1 Protein by ELISA Firstly, human PD-1 protein (purchased from Beijing BAPSIS, Cat No. PD1-H5221) was diluted to 1.5 μg/mL with PBS (purchased from Hyclone), and added into 96-well ELISA plate at 100 μl/well for antigen coating, and then incubated in a constant temperature incubator at 37° C. for 60 min. After the incubation, the plate was washed for three times, and PBS with 2% BSA was added at 200 μl/well for blocking, and incubated in a constant temperature incubator at 37° C. for 60 min. At the same time, the sample LL-VHH01-Fc and the control antibody LL-Pos were diluted with a diluent (PBS containing 2% BSA) to 100 μg/ml, and then diluted sequentially in a 3-fold gradient to 0.56 ng/ml in a sample dilution plate. The samples were then added to 96-well ELISA plates and incubated in a constant temperature incubator at 37° C. for 60 min. After the incubation, the plate was washed and the secondary antibody goat anti-human IgG (Fc specific)-HRP antibody (Sigma, Cat No. A-0170) was diluted at 6000-fold with 2% BSA, added to the ELISA plate at 100 μl/well and incubated in a constant temperature incubator at 37° C. for 30 min. After the incubation, the plate was washed for three times and a developing liquid, 100 μg/ml of TMB (3,3',5,5'-tetramethylbenzidine) was added at 100 μl/well and incubated in a constant temperature incubator at 37° C. for 15 min in darkness. Finally, a quenching solution (2 M/L hydrochloric acid solution) was added at 100 μl/well, the absorbance values were measured at 450 nm/620 nm using a micro-plate reader (Thermo Fisher Scientific, Varioskan LUX), and the data were analysed using Graphpad Prism.

Results are shown in FIG. 1, the $EC_{50}$ of LL-Pos binding PD-1 protein was 11.84 ng/ml. While the $EC_{50}$ of LL-VHH01-Fc was 29.69 ng/ml. Under such experimental condition, the upper plateau value of the dose-effect curve of LL-VHH01-Fc binding PD-1 protein was significantly higher than that of LL-Pos. Summing up, the affinity of the VHH Fc fusion protein of the present invention for PD-1 antigen was essentially comparable to that of the control antibody LL-Pos.

Example 6: Biological Activity of VHH-Fc Fusion Protein Using Luciferase Reporter Gene Assay CHO/PD-L1 cells (purchased from Promega) were cultured, digested, and resuspended in F-12 Nutrient Mixture Complete Medium containing 10% FBS, and cell density was adjusted to $5\times10^5$ cells/ml using Complete Medium based on cell counting results. Afterwards, the cell suspension was transferred to a loading tank and added to a 96-well plate at 100 μl/well using a multichannel pipette and placed in a 5% CO2 incubator at 37° C. for 16-22 h. Meanwhile, Jurkat/PD-1 cells (purchased from Promega) were cultured and cell density was adjusted to $2\times10^6$ cells/ml using analytical medium (RPMI 1640 Medium+2% FBS) based on cell counting results. The cell culture plate with CHO/PD-L1 cells was removed from the incubator and 100 μl of culture solution per well was removed using a multichannel pipette, followed by the addition of a sample to be tested, which was gradient-diluted (starting concentration of 1650 nM) at 40 μl/well. Then, the above Jurkat/PD-1 cell suspension was transferred to a loading tank and added into a cell culture plate at 40 μl/well, and then placed in a 5% CO2 incubator at 37° C. for 4-6 h. After the incubation, the cell culture plate was removed and placed at room temperature for 5-10 min, and then 40 μl of One-Glo reagent (purchased from Promega, Cat No. E6130) was added to each well and mixed on a mixer for 5-10 min, and then the chemiluminescence signal value were measured using a multifunctional microplate reader (Promega, Cat no. E6130), and the data were analysed using Graphpad Prism.

Figure 2:
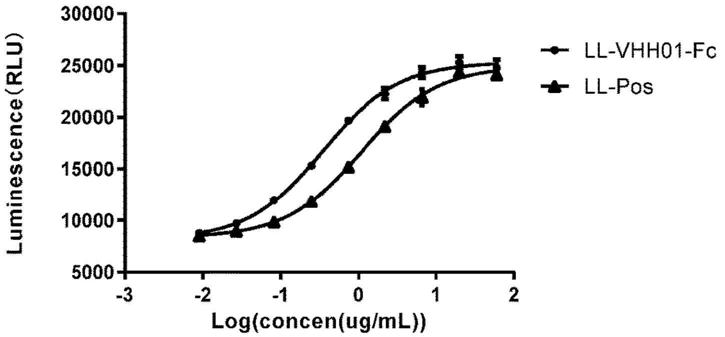
FIG. 2 shows results of bioactivity assay of VHH-Fc fusion protein, LL-VHH01-Fc blocking the binding of PD-L1 to PD-1 protein.

As shown in FIG. 2, LL-VHH01-Fc can effectively block the binding of PD-1 to PD-L1 and activated the downstream pathway to generate signals, and the $EC_{50}$ of the dose-effect curve was 0.35 μg/ml. The positive control, LL-Pos, can also effectively block the binding of PD-1 to PD-L1 and activated the downstream pathway to generate signals, and the $EC_{50}$ of the dose-effect curve was 1.09 μg/ml. ml. The results indicated that the ability of LL-VHH01-Fc to block the binding of PD-1 to PD-L1 was similar to that of the positive control.

The results of FIGS. 1 and 2 indicate that the PD-1 single domain antibody fusion proteins of the present invention are equal to or superior to the already marketed control antibodies in terms of affinity for the antigen PD-1 and blockade of the binding of PD-1 to PD-L1, and thus may be clinically more effective. In addition, single-domain antibodies have no light chain and are well suited as important constituent antibodies for the development of bis or multispecific antibody, which is expected to develop antibody drugs with better efficacy.

Example 7: Humanisation of Single Domain Antibody

LL-VHH01 was an alpaca-derived antibody, and LL-VHH01 was humanised in order to improve the drugability of this single domain antibody. Steps are listed below:

1. Antibody sequence alignment was performed using IMGT database. According to the results of sequence alignment in the database, IGHV3-23*04 was selected as the parent vector for LL-VHH01 humanisation;
2. CDR regions of LL-VHH01 single domain antibody were transplanted into IGHV3-23*04;
3. The transplanted humanised antibody was reverse-mutated to ensure the affinity of the humanised antibody.

Six candidate humanised antibodies were obtained:

>huVHH3-1

(SEQ ID NO: 14)
EVQLVESGGGLVQPGGSLRLSCAASGRTSSMYAMGWFRQAPGKGREFVAG
IGWENNTPYYARSVEGRFTISRDNVKNTVYLQMNSLRAEDTAVYYCAAQI
GISGTLGDYWGQGTQVTVSS

Nucleic acid sequence:

(SEQ ID NO: 15)
GAGGTGCAGCTTGTTGAAAGTGGTGGAGGTCTTGTTCAACCAGGGGGCTC
CCTCAGACTGTCTTGTGCGGCGAGCGGGCGGACATCCTCTATGTATGCGA
TGGGTTGGTTCCGACAGGCCCCCGGTAAAGGACGGGAGTTCGTAGCTGGC
ATCGGTTGGGAAAACAATACCCCTTATTACGCCCGGTCTGTTGAAGGTCG
ATTTACTATAAGTCGGGACAATGTGAAAAATACTGTCTATCTCCAAATGA
ACTCTCTGCGGGCCGAAGATACAGCGGTGTACTATTGTGCCGCCCAAATT
GGAATCAGCGGAACATTGGGTGATTATTGGGGCCAAGGTACGCAAGTTAC
AGTCTCCTCA

>huVHH3-2

(SEQ ID NO: 16)
EVQLVESGGGLVQPGGSLRLSCAASGRTSSMYAMGWFRQAPGNEREFVAG
IGWENNTPYYARSVEGRFTISRDNVKNTVYLQMNSLRAEDTAVYYCAAQI
GISGTLGDYWGQGTQVTVSS

Nucleic acid sequence:

(SEQ ID NO: 17)
GAAGTCCAACTGGTCGAAAGCGGCGGCGGTCTCGTCCAACCTGGAGGCTC
TCTTAGGTTGTCATGTGCCGCCTCAGGCAGAACATCCAGCATGTACGCAA
TGGGTTGGTTCAGACAGGCTCCGGGGAACGAGCGAGAATTCGTCGCGGGA
ATAGGATGGGAGAACAACACCCCATACTACGCACGCAGTGTGGAAGGCCG
ATTCACTATTAGTCGGGATAATGTTAAAAACACGGTCTACCTTCAAATGA
ACTCCCTTCGCGCAGAGGATACTGCAGTTTATTATTGCGCGGCCCAAATA
GGTATAAGTGGAACACTCGGGGACTACTGGGGCCAGGGAACACAGGTAAC
CGTATCATCA

>huVHH3-3

(SEQ ID NO: 18)
EVQLVESGGGLVQPGGSLRLSCAASGRTSSMYAMGWFRQAPGNEREFVAG
IGWENNTPYYARSVEGRFTISRDNVKNTVFLQMNRLRAEDTAVYYCAAQI
GISGTLGDYWGQGTQVTVSS

Nucleic acid sequence:

(SEQ ID NO: 19)
GAGGTCCAGTTGGTAGAAAGTGGTGGTGGGTTGGTGCAACCCGGTGGCTC
ATTGAGGCTGTCTTGTGCTGCGAGTGGCAGGACATCCTCTATGTATGCGA
TGGGATGGTTCCGACAAGCTCCAGGAAACGAGCGCGAGTTCGTAGCCGGA
ATTGGTTGGGAAAACAATACGCCCTATTATGCACGGTCTGTCGAGGGGAG
GTTCACTATCTCACGCGACAACGTCAAGAACACAGTGTTTCTTCAGATGA
ACCGACTCCGGGCGGAGGATACGGCCGTATATTATTGCGCAGCGCAAATC
GGTATATCCGGCACTCTTGGTGACTATTGGGGCCAGGGTACACAAGTGAC
AGTCTCTTCA

-continued

>huVHH3-4

(SEQ ID NO: 20)
EVQLVESGGGLVQPGGSLRLSCAASGRTSSMYAMGWFRQAPGNEREFVAG
IGWENNTPYYARSVEGRFTISRDNVKNTVFLQMNRLKPEDTAVYYCAAQI
GISGTLGDYWGQGTQVTVSS

Nucleic acid sequence:

(SEQ ID NO: 21)
GAAGTGCAACTCGTGGAGAGCGGGGGCGGACTTGTCCAACCGGGAGGGAG
TTTGAGACTCTCATGCGCCGCCTCTGGTAGAACTAGCAGCATGTACGCTA
TGGGATGGTTCAGGCAGGCTCCAGGGAACGAACGAGAATTCGTTGCAGGC
ATAGGATGGGAAAACAACACCCCATATTACGCTCGGTCCGTGGAAGGACG
ATTTACTATAAGCCGGGACAATGTAAAAAATACTGTCTTTCTCCAGATGA
ATAGGCTCAAGCCGGAGGATACAGCAGTTTATTATTGCGCTGCTCAAATT
GGGATTAGCGGGACCCTGGGTGACTATTGGGGGCAGGGAACGCAAGTGAC
TGTCAGTTCT

>huVHH3-5

(SEQ ID NO: 22)
ELQLVESGGGLVQAGGSLRLSCAASGRTSSMYAMGWFRQAPGNEREFVAG
IGWENNTPYYARSVEGRFTISRDNVKNTVFLQMNRLKPEDTAVYYCAAQI
GISGTLGDYWGQGTQVTVSS

Nucleic acid sequence:

(SEQ ID NO: 23)
GAGTTGCAACTGGTGGAAAGTGGTGGCGGGTTGGTTCAGGCAGGCGGTTC
CCTTCGCCTCTCCTGTGCGGCGAGTGGACGCACATCATCCATGTACGCAA
TGGGGTGGTTTCGACAAGCCCCCGGAAACGAACGCGAATTTGTTGCTGGG
ATTGGATGGGAAAACAATACGCCGTACTATGCCCGGAGCGTAGAAGGACG
ATTCACCATTTCCAGGGACAACGTCAAAAACACGGTCTTCTTGCAAATGA
ACCGCTTGAAACCAGAGGATACCGCAGTATACTATTGTGCTGCCCAGATC
GGCATATCAGGCACACTGGGCGACTATTGGGGCCAAGGGACCCAGGTCAC
TGTATCCAGC

>huVHH3-6

(SEQ ID NO: 24)
ELQLVESGGGLVQAGGSLRLSCAASGRTSSMYAMGWFRQAPGNEREFVAG
IGWENNTPYYARSVEGRFTISRDNVKNTVFLQMNRLKPEDAAVYFCAAQI
GISGTLGDYWGQGTQVTVSS

Nucleic acid sequence:

(SEQ ID NO: 25)
GAACTGCAACTCGTAGAATCTGGGGGTGGCTTGGTCCAGGCCGGGGGCAG
TCTGCGACTTTCCTGTGCCGCATCAGGAAGGACCTCCAGCATGTATGCGA
TGGGATGGTTCCGACAAGCTCCGGGAAATGAGCGCGAGTTTGTTGCGGGA
ATTGGCTGGGAGAATAACACGCCCTATTATGCTCGGTCCGTAGAGGGGAG
GTTCACTATCAGCCGAGATAATGTAAAAAACACCGTATTCCTCCAAATGA
ATCGGTTGAAACCAGAGGACGCAGCGGTCTACTTTTGCGCCGCGCAAATC
GGCATAAGCGGTACATTGGGGGATTACTGGGGTCAAGGCACACAGGTAAC
CGTCTCTAGT

Example 8: Preparation of Six Humanised Antibodies Labelled with Human IgG4 Fc

According to the experimental procedure of Example 3, six humanised antibodies fused with human IgG4 Fc tag were expressed, purified and named as: hu VHH3-1-Fc. hu VHH3-2-Fc, huVHH3-3-Fc. huVHH3-4-Fc, huVHH3-5-Fc, huVHH3-6-Fc. The sequences of six humanised anti-PD-1 single domain antibody fused with hIgG4 Fc are shown as below:

>huVHH3-1-Fc (SEQ ID NO: 26)

EVQLVESGGGLVQPGGSLRLSCAASGRTSSMYAMGWFRQAPGKGREFVAGIGWENNTPYYARS

VEGRFTISRDNVKNTVYLQMNSLRAEDTAVYYCAAQIGISGTLGDYWGQGTQVTVSSESKYGP

PCPPCPAPEFLGGPSVFLFPPKPKDTLMISRTPEVTCVVVDVSQEDPEVQFNWYVDGVEVHNA

KTKPREEQFNSTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRLTVD

KSRWQEGNVFSCSVMHEALHNHYTQKSLSLSLGK

Nucleic acid sequence:

(SEQ ID NO: 27)

GAGGTGCAGCTTGTTGAAAGTGGTGGAGGTCTTGTTCAACCAGGGGGCTCCCTCAGACTGTCT

TGTGCGGCGAGCGGGCGGACATCCTCTATGTATGCGATGGGTTGGTTCCGACAGGCCCCCGGT

AAAGGACGGGAGTTCGTAGCTGGCATCGGTTGGGAAAACAATACCCCTTATTACGCCCGGTCT

GTTGAAGGTCGATTTACTATAAGTCGGGACAATGTGAAAAATACTGTCTATCTCCAAATGAAC

TCTCTGCGGGCCGAAGATACAGCGGTGTACTATTGTGCCGCCCAAATTGGAATCAGCGGAACA

TTGGGTGATTATTGGGGCCAAGGTACGCAAGTTACAGTCTCCTCAGAGTCCAAATATGGTCCC

CCATGCCCACCATGCCCAGCACCTGAGTTCCTGGGGGGACCATCAGTCTTCCTGTTCCCCCCA

AAACCCAAGGACACTCTCATGATCTCCCGGACCCCTGAGGTCACGTGCGTGGTGGTGGACGTG

AGCCAGGAAGACCCCGAGGTCCAGTTCAACTGGTACGTGGATGGCGTGGAGGTGCATAATGCC

AAGACAAAGCCGCGGGAGGAGCAGTTCAACAGCACGTACCGTGTGGTCAGCGTCCTCACCGTC

CTGCACCAGGACTGGCTGAACGGCAAGGAGTACAAGTGCAAGGTCTCCAACAAAGGCCTCCCG

TCCTCCATCGAGAAAACCATCTCCAAAGCCAAAGGGCAGCCCCGAGAGCCACAGGTGTACACC

CTGCCCCCATCCCAGGAGGAGATGACCAAGAACCAGGTCAGCCTGACCTGCCTGGTCAAAGGC

TTCTACCCCAGCGACATCGCCGTGGAGTGGGAGAGCAATGGGCAGCCGGAGAACAACTACAAG

ACCACGCCTCCCGTGCTGGACTCCGACGGCTCCTTCTTCCTCTACAGCAGGCTAACCGTGGAC

AAGAGCAGGTGGCAGGAGGGGAATGTCTTCTCATGCTCCGTGATGCATGAGGCTCTGCACAAC

CACTACACACAGAAGAGCCTCTCCCTGTCTCTGGGTAAA

>huVHH3-2-Fc (SEQ ID NO: 28)

EVQLVESGGGLVQPGGSLRLSCAASGRTSSMYAMGWFRQAPGNEREFVAGIGWENNTPYYARS

VEGRFTISRDNVKNTVYLQMNSLRAEDTAVYYCAAQIGISGTLGDYWGQGTQVTVSSESKYGP

PCPPCPAPEFLGGPSVFLFPPKPKDTLMISRTPEVTCVVVDVSQEDPEVQFNWYVDGVEVHNA

KTKPREEQFNSTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRLTVD

KSRWQEGNVFSCSVMHEALHNHYTQKSLSLSLGK

Nucleic acid sequence:

(SEQ ID NO: 29)

GAAGTCCAACTGGTCGAAAGCGGCGGCGGTCTCGTCCAACCTGGAGGCTCTCTTAGGTTGTCA

TGTGCCGCCTCAGGCAGAACATCCAGCATGTACGCAATGGGTTGGTTCAGACAGGCTCCGGGG

AACGAGCGAGAATTCGTCGCGGGAATAGGATGGGAGAACAACACCCCATACTACGCACGCAGT

GTGGAAGGCCGATTCACTATTAGTCGGGATAATGTTAAAAACACGGTCTACCTTCAAATGAAC

-continued

TCCCTTCGCGCAGAGGATACTGCAGTTTATTATTGCGCGGCCCAAATAGGTATAAGTGGAACA

CTCGGGGACTACTGGGGCCAGGGAACACAGGTAACCGTATCATCAGAGTCCAAATATGGTCCC

CCATGCCCACCATGCCCAGCACCTGAGTTCCTGGGGGGACCATCAGTCTTCCTGTTCCCCCCA

AAACCCAAGGACACTCTCATGATCTCCCGGACCCCTGAGGTCACGTGCGTGGTGGTGGACGTG

AGCCAGGAAGACCCCGAGGTCCAGTTCAACTGGTACGTGGATGGCGTGGAGGTGCATAATGCC

AAGACAAAGCCGCGGGAGGAGCAGTTCAACAGCACGTACCGTGTGGTCAGCGTCCTCACCGTC

CTGCACCAGGACTGGCTGAACGGCAAGGAGTACAAGTGCAAGGTCTCCAACAAAGGCCTCCCG

TCCTCCATCGAGAAAACCATCTCCAAAGCCAAAGGGCAGCCCCGAGAGCCACAGGTGTACACC

CTGCCCCCATCCCAGGAGGAGATGACCAAGAACCAGGTCAGCCTGACCTGCCTGGTCAAAGGC

TTCTACCCCAGCGACATCGCCGTGGAGTGGGAGAGCAATGGGCAGCCGGAGAACAACTACAAG

ACCACGCCTCCCGTGCTGGACTCCGACGGCTCCTTCTTCCTCTACAGCAGGCTAACCGTGGAC

AAGAGCAGGTGGCAGGAGGGGAATGTCTTCTCATGCTCCGTGATGCATGAGGCTCTGCACAAC

CACTACACACAGAAGAGCCTCTCCCTGTCTCTGGGTAAA

>huVHH3-3-Fc (SEQ ID NO: 30)

EVQLVESGGGLVQPGGSLRLSCAASGRTSSMYAMGWFRQAPGNEREFVAGIGWENNTPYYARS

VEGRFTISRDNVKNTVFLQMNRLRAEDTAVYYCAAQIGISGTLGDYWGQGTQVTVSSESKYGP

PCPPCPAPEFLGGPSVFLFPPKPKDTLMISRTPEVTCVVVDVSQEDPEVQFNWYVDGVEVHNA

KTKPREEQFNSTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRLTVD

KSRWQEGNVFSCSVMHEALHNHYTQKSLSLSLGK

Nucleic acid sequence:

(SEQ ID NO: 31)

GAGGTCCAGTTGGTAGAAAGTGGTGGTGGGTTGGTGCAACCCGGTGGCTCATTGAGGCTGTCT

TGTGCTGCGAGTGGCAGGACATCCTCTATGTATGCGATGGGATGGTTCCGACAAGCTCCAGGA

AACGAGCGCGAGTTCGTAGCCGGAATTGGTTGGGAAAACAATACGCCCTATTATGCACGGTCT

GTCGAGGGGAGGTTCACTATCTCACGCGACAACGTCAAGAACACAGTGTTTCTTCAGATGAAC

CGACTCCGGGCGGAGGATACGGCCGTATATTATTGCGCAGCGCAAATCGGTATATCCGGCACT

CTTGGTGACTATTGGGGCCAGGGTACACAAGTGACAGTCTCTTCAGAGTCCAAATATGGTCCC

CCATGCCCACCATGCCCAGCACCTGAGTTCCTGGGGGGACCATCAGTCTTCCTGTTCCCCCCA

AAACCCAAGGACACTCTCATGATCTCCCGGACCCCTGAGGTCACGTGCGTGGTGGTGGACGTG

AGCCAGGAAGACCCCGAGGTCCAGTTCAACTGGTACGTGGATGGCGTGGAGGTGCATAATGCC

AAGACAAAGCCGCGGGAGGAGCAGTTCAACAGCACGTACCGTGTGGTCAGCGTCCTCACCGTC

CTGCACCAGGACTGGCTGAACGGCAAGGAGTACAAGTGCAAGGTCTCCAACAAAGGCCTCCCG

TCCTCCATCGAGAAAACCATCTCCAAAGCCAAAGGGCAGCCCCGAGAGCCACAGGTGTACACC

CTGCCCCCATCCCAGGAGGAGATGACCAAGAACCAGGTCAGCCTGACCTGCCTGGTCAAAGGC

TTCTACCCCAGCGACATCGCCGTGGAGTGGGAGAGCAATGGGCAGCCGGAGAACAACTACAAG

ACCACGCCTCCCGTGCTGGACTCCGACGGCTCCTTCTTCCTCTACAGCAGGCTAACCGTGGAC

AAGAGCAGGTGGCAGGAGGGGAATGTCTTCTCATGCTCCGTGATGCATGAGGCTCTGCACAAC

CACTACACACAGAAGAGCCTCTCCCTGTCTCTGGGTAAA

>huVHH3-4-Fc (SEQ ID NO: 32)

EVQLVESGGGLVQPGGSLRLSCAASGRTSSMYAMGWFRQAPGNEREFVAGIGWENNTPYYARS

VEGRFTISRDNVKNTVFLQMNRLKPEDTAVYYCAAQIGISGTLGDYWGQGTQVTVSSESKYGP

-continued

PCPPCPAPEFLGGPSVFLFPPKPKDTLMISRTPEVTCVVVDVSQEDPEVQFNWYVDGVEVHNA

KTKPREEQFNSTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRLTVD

KSRWQEGNVFSCSVMHEALHNHYTQKSLSLSLGK

Nucleic acid sequence:

(SEQ ID NO: 33)

GAAGTGCAACTCGTGGAGAGCGGGGGCGGACTTGTCCAACCGGGAGGGAGTTTGAGACTCTCA

TGCGCCGCCTCTGGTAGAACTAGCAGCATGTACGCTATGGGATGGTTCAGGCAGGCTCCAGGG

AACGAACGAGAATTCGTTGCAGGCATAGGATGGGAAAACAACACCCCATATTACGCTCGGTCC

GTGGAAGGACGATTTACTATAAGCCGGGACAATGTAAAAAATACTGTCTTTCTCCAGATGAAT

AGGCTCAAGCCGGAGGATACAGCAGTTTATTATTGCGCTGCTCAAATTGGGATTAGCGGGACC

CTGGGTGACTATTGGGGGCAGGGAACGCAAGTGACTGTCAGTTCTGAGTCCAAATATGGTCCC

CCATGCCCACCATGCCCAGCACCTGAGTTCCTGGGGGGACCATCAGTCTTCCTGTTCCCCCCA

AAACCCAAGGACACTCTCATGATCTCCCGGACCCCTGAGGTCACGTGCGTGGTGGTGGACGTG

AGCCAGGAAGACCCCGAGGTCCAGTTCAACTGGTACGTGGATGGCGTGGAGGTGCATAATGCC

AAGACAAAGCCGCGGGAGGAGCAGTTCAACAGCACGTACCGTGTGGTCAGCGTCCTCACCGTC

CTGCACCAGGACTGGCTGAACGGCAAGGAGTACAAGTGCAAGGTCTCCAACAAAGGCCTCCCG

TCCTCCATCGAGAAAACCATCTCCAAAGCCAAAGGGCAGCCCCGAGAGCCACAGGTGTACACC

CTGCCCCCATCCCAGGAGGAGATGACCAAGAACCAGGTCAGCCTGACCTGCCTGGTCAAAGGC

TTCTACCCCAGCGACATCGCCGTGGAGTGGGAGAGCAATGGGCAGCCGGAGAACAACTACAAG

ACCACGCCTCCCGTGCTGGACTCCGACGGCTCCTTCTTCCTCTACAGCAGGCTAACCGTGGAC

AAGAGCAGGTGGCAGGAGGGGAATGTCTTCTCATGCTCCGTGATGCATGAGGCTCTGCACAAC

CACTACACACAGAAGAGCCTCTCCCTGTCTCTGGGTAAA

>huVHH3-5-Fc (SEQ ID NO: 34)

ELQLVESGGGLVQAGGSLRLSCAASGRTSSMYAMGWFRQAPGNEREFVAGIGWENNTPYYARS

VEGRFTISRDNVKNTVFLQMNRLKPEDTAVYYCAAQIGISGTLGDYWGQGTQVTVSSESKYGP

PCPPCPAPEFLGGPSVFLFPPKPKDTLMISRTPEVTCVVVDVSQEDPEVQFNWYVDGVEVHNA

KTKPREEQFNSTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRLTVD

KSRWQEGNVFSCSVMHEALHNHYTQKSLSLSLGK

Nucleic acid sequence:

(SEQ ID NO: 35)

GAGTTGCAACTGGTGGAAAGTGGTGGCGGGTTGGTTCAGGCAGGCGGTTCCCTTCGCCTCTCC

TGTGCGGCGAGTGGACGCACATCATCCATGTACGCAATGGGGTGGTTTCGACAAGCCCCCGGA

AACGAACGCGAATTTGTTGCTGGGATTGGATGGGAAAACAATACGCCGTACTATGCCCGGAGC

GTAGAAGGACGATTCACCATTTCCAGGGACAACGTCAAAAACACGGTCTTCTTGCAAATGAAC

CGCTTGAAACCAGAGGATACCGCAGTATACTATTGTGCTGCCCAGATCGGCATATCAGGCACA

CTGGGCGACTATTGGGGCCAAGGGACCCAGGTCACTGTATCCAGCGAGTCCAAATATGGTCCC

CCATGCCCACCATGCCCAGCACCTGAGTTCCTGGGGGGACCATCAGTCTTCCTGTTCCCCCCA

AAACCCAAGGACACTCTCATGATCTCCCGGACCCCTGAGGTCACGTGCGTGGTGGTGGACGTG

AGCCAGGAAGACCCCGAGGTCCAGTTCAACTGGTACGTGGATGGCGTGGAGGTGCATAATGCC

AAGACAAAGCCGCGGGAGGAGCAGTTCAACAGCACGTACCGTGTGGTCAGCGTCCTCACCGTC

-continued

```
CTGCACCAGGACTGGCTGAACGGCAAGGAGTACAAGTGCAAGGTCTCCAACAAAGGCCTCCCG

TCCTCCATCGAGAAAACCATCTCCAAAGCCAAAGGGCAGCCCCGAGAGCCACAGGTGTACACC

CTGCCCCCATCCCAGGAGGAGATGACCAAGAACCAGGTCAGCCTGACCTGCCTGGTCAAAGGC

TTCTACCCCAGCGACATCGCCGTGGAGTGGGAGAGCAATGGGCAGCCGGAGAACAACTACAAG

ACCACGCCTCCCGTGCTGGACTCCGACGGCTCCTTCTTCCTCTACAGCAGGCTAACCGTGGAC

AAGAGCAGGTGGCAGGAGGGGAATGTCTTCTCATGCTCCGTGATGCATGAGGCTCTGCACAAC

CACTACACACAGAAGAGCCTCTCCCTGTCTCTGGGTAAA

>huVHH3-6-Fc
                                                    (SEQ ID NO: 36)
ELQLVESGGGLVQAGGSLRLSCAASGRTSSMYAMGWFRQAPGNEREFVAGIGWENNTPYYARS

VEGRFTISRDNVKNTVFLQMNRLKPEDAAVYFCAAQIGISGTLGDYWGQGTQVTVSSESKYGP

PCPPCPAPEFLGGPSVFLFPPKPKDTLMISRTPEVTCVVVDVSQEDPEVQFNWYVDGVEVHNA

KTKPREEQFNSTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRLTVD

KSRWQEGNVFSCSVMHEALHNHYTQKSLSLSLGK

Nucleic acid sequence:
                                                    (SEQ ID NO: 37)
GAACTGCAACTCGTAGAATCTGGGGGTGGCTTGGTCCAGGCCGGGGGCAGTCTGCGACTTTCC

TGTGCCGCATCAGGAAGGACCTCCAGCATGTATGCGATGGGATGGTTCCGACAAGCTCCGGGA

AATGAGCGCGAGTTTGTTGCGGGAATTGGCTGGGAGAATAACACGCCCTATTATGCTCGGTCC

GTAGAGGGGAGGTTCACTATCAGCCGAGATAATGTAAAAAACACCGTATTCCTCCAAATGAAT

CGGTTGAAACCAGAGGACGCAGCGGTCTACTTTTGCGCCGCGCAAATCGGCATAAGCGGTACA

TTGGGGGATTACTGGGGTCAAGGCACACAGGTAACCGTCTCTAGTGAGTCCAAATATGGTCCC

CCATGCCCACCATGCCCAGCACCTGAGTTCCTGGGGGGACCATCAGTCTTCCTGTTCCCCCCA

AAACCCAAGGACACTCTCATGATCTCCCGGACCCCTGAGGTCACGTGCGTGGTGGTGGACGTG

AGCCAGGAAGACCCCGAGGTCCAGTTCAACTGGTACGTGGATGGCGTGGAGGTGCATAATGCC

AAGACAAAGCCGCGGGAGGAGCAGTTCAACAGCACGTACCGTGTGGTCAGCGTCCTCACCGTC

CTGCACCAGGACTGGCTGAACGGCAAGGAGTACAAGTGCAAGGTCTCCAACAAAGGCCTCCCG

TCCTCCATCGAGAAAACCATCTCCAAAGCCAAAGGGCAGCCCCGAGAGCCACAGGTGTACACC

CTGCCCCCATCCCAGGAGGAGATGACCAAGAACCAGGTCAGCCTGACCTGCCTGGTCAAAGGC

TTCTACCCCAGCGACATCGCCGTGGAGTGGGAGAGCAATGGGCAGCCGGAGAACAACTACAAG

ACCACGCCTCCCGTGCTGGACTCCGACGGCTCCTTCTTCCTCTACAGCAGGCTAACCGTGGAC

AAGAGCAGGTGGCAGGAGGGGAATGTCTTCTCATGCTCCGTGATGCATGAGGCTCTGCACAAC

CACTACACACAGAAGAGCCTCTCCCTGTCTCTGGGTAAA
```

Example 9: Detection of Affinity of Humanised Antibodies for Antigen PD-1

Figure 3:
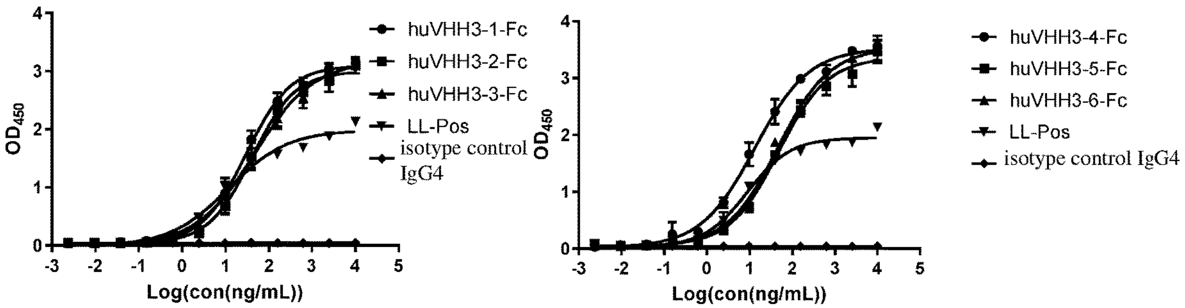
FIG. 3 shows that all of 6 humanized antibodies can bind PD-1 antigen well.

According to the experimental procedure of Example 5, the affinity of the humanised antibody for the antigen PD-1 was tested. The results of the assay are shown in FIG. 3. The results show that the $EC_{50}$ of huVHH3-1-Fc, huVHH3-2-Fc, huVHH3-3-Fc, hu VHH3-4-Fc, huVHH3-5-Fc, and huVHH3-6-Fc binding to the PD-1 protein were 29.25 ng/ml, 40.50 ng/ml, 46.96 ng/ml, 13.31 ng/ml, 47.61 ng/ml and 45.97 ng/ml, respectively. The experimental results indicated that the affinity of the six humanised antibodies was similar to or better than that of the parent antibody after humanisation.

Figure 4:
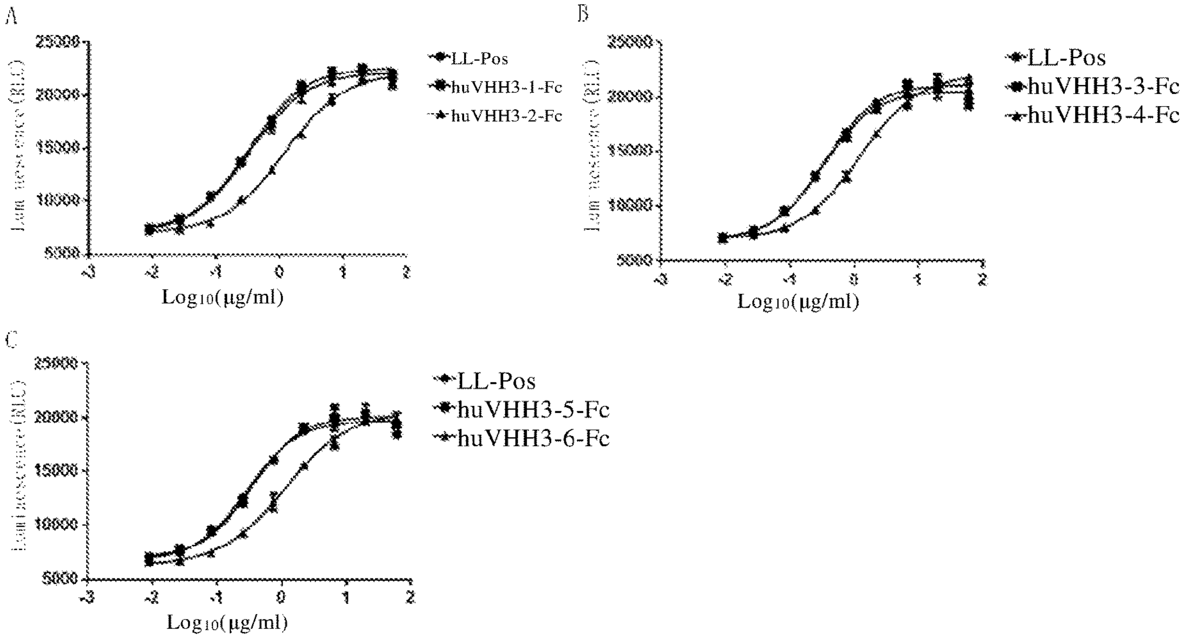
FIG. 4 shows that the 6 humanized antibodies can block the PD-1 and PD-L1 signaling pathways well at the cellular level.

Example 10: Detection of Cellular Activity of Humanised Antibodies Blocking PD-1/PD-L1 Signalling Pathway In Vitro According to the experimental procedure of Example 6, the cellular activity of the humanised antibodies in blocking the PD-1/PD-L1 signalling pathway in vitro was tested. The results of the assay are shown in FIG. 4. The results indicate that the six humanised antibodies exhibited similar or better biological effects than the parent antibodies at the cellular level in vitro after humanisation.

Example 11: Affinity Determination of Six Humanised Antibodies

An Octet RED 96e molecular interaction analyser from Fortebio was used in this experiment. Candidate antibody molecules were first captured separately (at a concentration of 5 μg/mL) using Protein A probe (Fortebio). The probes were then immersed in a 30 nM or 120 nM human PD-1 antigen solution, respectively, so that the candidate antibody molecules can bind to the antigen for 180 s. Then the probes were immersed in a buffer for a dissociation time of 1400 s, and the binding and dissociation signals were measured. Binding dissociation curves were fitted using the software Octet data analysis software to determine the affinity KD values.

The experiment results are shown in Table 4, which indicate that all six PD-1 single-domain recombinant antibodies can bind the antigen with high affinity and the affinity for binding antigen varies little.

TABLE 4

Binding of six humanised PD-1 recombinant antibodies to antigen

| Antigen | kon (1/Ms) | kdis (1/s) | KD (M) |
|---|---|---|---|
| LL-VHH01-Fc | 7.94E+04 | 2.01E−04 | 2.53E−09 |
| hu-VHH3-1-Fc | 8.40E+04 | 2.40E−04 | 2.86E−09 |
| hu-VHH3-2-Fc | 7.91E+04 | 2.31E−04 | 2.92E−09 |
| hu-VHH3-3-Fc | 8.91E+04 | 2.22E−04 | 2.49E−09 |
| hu-VHH3-4-Fc | 7.45E+04 | 3.08E−04 | 4.13E−09 |
| hu-VHH3-5-Fc | 8.46E+04 | 2.25E−04 | 2.66E−09 |
| hu-VHH3-6-Fc | 9.42E+04 | 2.67E−04 | 2.83E−09 |

Example 12: In Vivo Pharmacodynamic Evaluation of Humanised PD-1 Single Domain Antibodies 50 6-8-week-old female hPD-1 C57 (PD-1 gene humanized) humanized mice (Baiosetu) were taken, and MC38 WT cells were inoculated into the right subcutaneous side of the mice at a concentration of $1\times10^6$ cells/0.1 mL, and when the tumour had grown to approximately 100 $mm^3$, the mice were randomly grouped according to the volume of the tumor, with 5 mice in each group and a total of 8 groups, respectively:

Group 1 KLH IgG4 (0.3 mg/kg) negative control group, Group 2 LL-Pos (0.3 mg/kg) positive control group, Group 3 huVHH3-1-Fc (0.3 mg/kg) treatment group, Group 4 huVHH3-3-Fc (0.3 mg/kg) treatment group, and Group 5 huVHH3-5-Fc (0.3 mg/kg) treatment group.

The administration route for all groups was intraperitoneal injection at a dose of 0.3 mg/kg and a concentration of 0.03 mg/ml. The drug was administered twice a week for 5 consecutive doses, and the experiment was stopped 3 days after the last dose. The tumor volume and body weight were measured twice a week, and mice body weight and tumor volume were recorded. Mice were euthanised at the end of the experiment and the relative tumour inhibition rate TGI %=(1−(Ti−T0)/(Vi−V0))×100% was calculated. (Ti: mean tumor volume of the treatment group or positive control group on day i of drug administration; T0: mean tumor volume of the treatment group or positive control group on day 0 of drug administration; Vi: mean tumor volume of the negative control group on day i of drug administration; V0: mean tumor volume of the negative control group on day 0 of drug administration).

Figure 5:
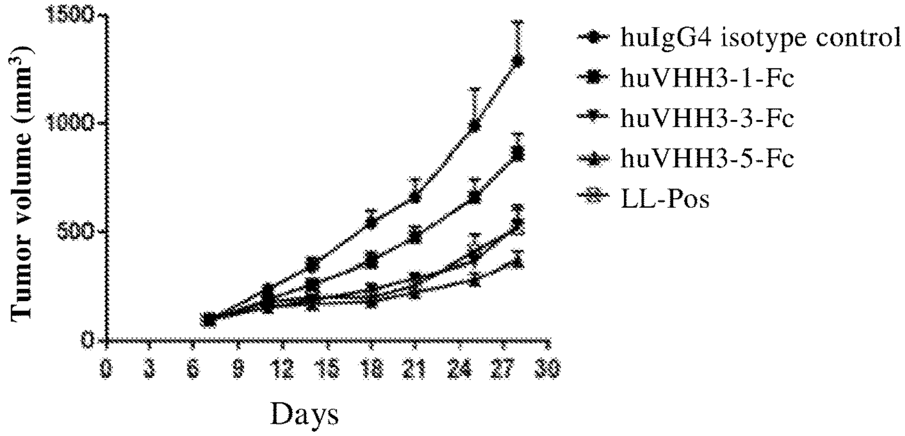
FIG. 5 shows that 3 representative humanized antibodies can control tumor growth well in animals.

As shown in FIG. 5, on day 28 after the mice were inoculated with tumor cells, the average tumor volume in the negative control group was 1375±115 $mm^3$, and the average tumor volume in the positive control group was 494±267 $mm^3$. The relative tumor inhibition rate was 69.10% compared with that in the negative control group. The average tumor volumes in the treatment Group 3, 4 and 5 were 823±85 $mm^3$, 483±197 $mm^3$ and 320±229 $mm^3$. The relative tumor inhibition rates are 43.30%, 70.00% and 82.75% compared with that in the negative control group, respectively, suggesting that the above humanized anti-PD-1 single-domain antibody was able to in vivo inhibit the growth of subcutaneous transplantation tumors of MC38-WT cells in hPD-1 humanized mouse, and was similar to or significantly superior to the positive control antibody.

Example 13: Detection on Chemical and Serum Stability of Representative Humanised Antibodies The candidate molecules were moved into a pH 5.5 buffer (20 mM acetic acid-sodium acetate, 220 mM alginate, 0.02% polysorbate 80), the sample concentration was controlled around 10 mg/ml, a certain volume of sample was dispensed (200 μl/tube) and placed in a 40° C. incubator to investigate the stability at 0, 2 and 4 weeks. Samples were sent and tested according to the time points for the purity of SEC-HPLC and the binding ELISA activity. The results showed that the three candidate molecules had good chemical stability, and there was no significant decrease in monomer purity and binding ELISA activity, as shown in Table 5.

TABLE 5

Detection on chemical stability of three representative humanised antibodies

| | 0 week | | | | 2 week | | | | 4 week | | | |
|---|---|---|---|---|---|---|---|---|---|---|---|---|
| | SEC-HPLC | | | ELISA | SEC-HPLC | | | ELISA | SEC-HPLC | | | ELISA |
| Sample | polymer % | monomer % | fragment % | binding (%) | polymer % | monomer % | fragment % | binding (%) | polymer % | monomer % | fragment % | binding (%) |
| huVHH3-1-Fc | 3.2 | 96.2 | 0.6 | 111.2 | 2.2 | 97.3 | 0.4 | 105.7 | 2.6 | 97.2 | 0.1 | 97.1 |
| huVHH3-3-Fc | 5.1 | 94.5 | 0.4 | 121.3 | 4.0 | 95.6 | 0.4 | 102.9 | 2.9 | 96.9 | 0.2 | 92.9 |
| huVHH3-5-Fc | 6.9 | 92.8 | 0.3 | 93.9 | 3.9 | 95.5 | 0.6 | 103.5 | 2.4 | 97.3 | 0.2 | 86.5 |

The candidate molecules were added into human serum, and the sample concentration was controlled to be around 1 mg/ml, and a certain volume of sample (200 μl/tube) was dispensed and placed in a 37° C. incubator to investigate the stability at 0, 2 and 4 weeks. Samples were sent and tested for the binding ELISA activity according to the time points. The results showed that the three candidate molecules had good serum stability and the binding ELISA activity did not show significant decrease, as shown in Table 6.

TABLE 6

| Detection on serum stability for three representative humanised antibodies | | | |
|---|---|---|---|
| Sample | 0 week ELISA binding(%) | 2 week ELISA binding(%) | 4 week ELISA binding(%) |
| huVHH3-1-Fc | 107.5 | 98.7 | 97.8 |
| huVHH3-3-Fc | 99.0 | 92.2 | 101.5 |
| huVHH3-5-Fc | 82.4 | 82.3 | 87.3 |

The above results indicate that the PD-1 humanised single domain antibodies in the present invention have excellent chemical and serum stability for subsequent development.

All documents mentioned in the present invention are cited as references in the present application as if each document was cited individually as a reference. It is further to be understood that after reading the above teachings of the present invention, a skilled person may make various alterations or modifications to the present invention, and these equivalent forms will fall within the scope of the claims appended to the present application.

The invention claimed is:

1. A single domain antibody targeting PD-1, wherein said single domain antibody comprises CDR1 shown in SEQ ID NO: 2, CDR2 shown in SEQ ID NO: 3 and CDR3 shown in SEQ ID NO: 4.

2. A humanized single domain antibody targeting PD-1, wherein the framework regions FR1, FR2, FR3 and FR4 are humanized based on the single domain antibody of claim 1.

3. An antibody targeting PD-1, wherein said antibody comprises one or more single domain antibodies targeting PD-1 of claim 1 or humanized single domain antibodies targeting PD-1, wherein the framework regions FR1, FR2, FR3 and FR4 of the humanized single domain antibody are humanized based on the single domain antibody of claim 1.

4. A bispecific antibody, wherein said bispecific antibody comprises a first antibody and a second antibody, said first antibody comprises a single domain antibody targeting PD-1 of claim 1, a humanized single-domain antibody targeting PD-1, or an antibody targeting PD-1;

wherein the framework regions FR1, FR2, FR3 and FR4 of the humanized single-domain antibody are humanized based on the single domain antibody of claim 1; and the antibody targeting PD-1 comprises one or more single domain antibodies targeting PD-1 of claim 1 or the humanized single domain antibodies.

5. A fusion protein, wherein said fusion protein comprises a single-domain antibody targeting PD-1 of claim 1, a humanized single-domain antibody targeting PD-1, or an antibody targeting PD-1, an optional linking sequence, and an Fc fragment of an immunoglobulin;

wherein the framework regions FR1, FR2, FR3 and FR4 of the humanized single-domain antibody are humanized based on the single domain antibody of claim 1; and the antibody targeting PD-1 comprises one or more single domain antibodies targeting PD-1 of claim 1 or the humanized single domain antibodies.

6. A nucleic acid molecule, wherein said nucleic acid molecule encodes a single-domain antibody targeting PD-1 of claim 1, a humanized single-domain antibody targeting PD-1, an antibody targeting PD-1, a bispecific antibody, or a fusion protein;

wherein the framework regions FR1, FR2, FR3 and FR4 of the humanized single-domain antibody are humanized based on the single domain antibody of claim 1;

the antibody targeting PD-1 comprises one or more single domain antibodies targeting PD-1 of claim 3 or the humanized single domain antibodies;

the bispecific antibody comprises a first antibody and a second antibody, said first antibody comprises a single domain antibody targeting PD-1 of claim 1, the humanized single-domain antibody targeting PD-1, or the antibody targeting PD-1; and the fusion protein comprises a single-domain antibody targeting PD-1 of claim 1, the humanized single-domain antibody targeting PD-1, or the antibody targeting PD-1, an optional linking sequence, and an Fc fragment of an immunoglobulin.

7. An expression vector, wherein said expression vector comprises a nucleic acid molecule of claim 6.

8. A host cell, wherein said host cell comprises an expression vector, or having a nucleic acid molecule of claim 6 integrated into its genome, and said expression vector comprises a nucleic acid molecule of claim 6.

9. A method for preparing a single-domain antibody targeting PD-1 of claim 1, a humanized a single-domain antibody targeting PD-1, an antibody targeting PD-1, a bispecific antibody, or a fusion protein, wherein said method comprises steps of:

1) culturing a host cell under suitable conditions, thereby obtaining a culture containing said VHH chain of a single-domain antibody targeting PD-1, heavy chain variable region of an antibody targeting PD-1, single-domain antibody targeting PD-1, humanized VHH chain of a single-domain antibody targeting PD-1, antibody targeting PD-1, bispecific antibody or fusion protein; and 2) optionally, isolating or recovering said single-domain antibody targeting PD-1, humanized single-domain antibody targeting PD-1, antibody targeting PD-1, bispecific antibody or fusion protein from said culture;

wherein the framework regions FR1, FR2, FR3 and FR4 of the humanized single-domain antibody are humanized based on the single domain antibody of claim 1;

the antibody targeting PD-1 comprises one or more single domain antibodies targeting PD-1 of claim 1 or the humanized single domain antibodies;

the bispecific antibody comprises a first antibody and a second antibody, said first antibody comprises a single domain antibody targeting PD-1 of claim 1, the humanized single-domain antibody targeting PD-1, or the antibody targeting PD-1;

the fusion protein comprises a single-domain antibody targeting PD-1 of claim 1, the humanized single-domain antibody targeting PD-1, or the antibody targeting PD-1, an optional linking sequence, and an Fc fragment of an immunoglobulin; and the host cell comprises an expression vector comprising a nucleic acid molecule, or having the nucleic acid molecule integrated into its genome, and the nucleic acid molecule encodes the single-domain antibody targeting PD-1 of claim 1, the humanized single-domain antibody targeting PD-1, the antibody targeting PD-1, the bispecific antibody, or the fusion protein.

10. An immunoconjugate, wherein said immunoconjugate comprises:

1) a single-domain antibody targeting PD-1 of claim 1, a humanized a single-domain antibody targeting PD-1, an antibody targeting PD-1, a bispecific antibody, or a fusion protein; and 2) a conjugated moiety selected from a detectable marker, drug, toxin, cytokine, radionuclide, or enzyme;

wherein the framework regions FR1, FR2, FR3 and FR4 of the humanized single-domain antibody are humanized based on the single domain antibody of claim 1;

the antibody targeting PD-1 comprises one or more single domain antibodies targeting PD-1 of claim 1 or the humanized single domain antibodies;

the bispecific antibody comprises a first antibody and a second antibody, said first antibody comprises a single domain antibody targeting PD-1 of claim 1, the humanized single-domain antibody targeting PD-1, or the antibody targeting PD-1; and the fusion protein comprises a single-domain antibody targeting PD-1 of claim 1, the humanized single-domain antibody targeting PD-1, or the antibody targeting PD-1, an optional linking sequence, and an Fc fragment of an immunoglobulin.

11. A pharmaceutical composition, wherein said pharmaceutical composition comprises a therapeutically or diagnostically effective amount of a single-domain antibody targeting PD-1 of claim 1, a humanized single-domain antibody targeting PD-1, an antibody targeting PD-1, a bispecific antibody, or a fusion protein or an immunoconjugate, and optionally a pharmaceutically acceptable excipient;

wherein the framework regions FR1, FR2, FR3 and FR4 of the humanized single-domain antibody are humanized based on the single domain antibody of claim 1;

the antibody targeting PD-1 comprises one or more single domain antibodies targeting PD-1 of claim 1 or the humanized single domain antibodies;

the bispecific antibody comprises a first antibody and a second antibody, said first antibody comprises a single domain antibody targeting PD-1 of claim 1, the humanized single-domain antibody targeting PD-1, or the antibody targeting PD-1;

the fusion protein comprises a single-domain antibody targeting PD-1 of claim 1, the humanized single-domain antibody targeting PD-1, or the antibody targeting PD-1, an optional linking sequence, and an Fc fragment of an immunoglobulin; and the immunoconjugate comprises a single-domain antibody targeting PD-1 of claim 1, the humanized single-domain antibody targeting PD-1, the antibody targeting PD-1, the bispecific antibody, or the fusion protein; and a conjugated moiety selected from a detectable marker, drug, toxin, cytokine, radionuclide, or enzyme.

12. A kit, wherein said kit comprises:

1) a single-domain antibody targeting PD-1 of claim 1, a humanized single-domain antibody targeting PD-1, an antibody targeting PD-1, a bispecific antibody, or a fusion protein, an immunoconjugate, or a pharmaceutical composition;

2) a container; and

3) Optionally, an instruction;

wherein the framework regions FR1, FR2, FR3 and FR4 of the humanized single-domain antibody are humanized based on the single domain antibody of claim 1;

the antibody targeting PD-1 comprises one or more single domain antibodies targeting PD-1 of claim 1 or the humanized single domain antibodies;

the bispecific antibody comprises a first antibody and a second antibody, said first antibody comprises a single domain antibody targeting PD-1 of claim 1, the humanized single-domain antibody targeting PD-1, or the antibody targeting PD-1;

the fusion protein comprises a single-domain antibody targeting PD-1 of claim 1, the humanized single-domain antibody targeting PD-1, or the antibody targeting PD-1, an optional linking sequence, and an Fc fragment of an immunoglobulin;

the immunoconjugate comprises a single-domain antibody targeting PD-1 of claim 1, the humanized single-domain antibody targeting PD-1, the antibody targeting PD-1, the bispecific antibody, or the fusion protein; and a conjugated moiety selected from a detectable marker, drug, toxin, cytokine, radionuclide, or enzyme; and the pharmaceutical composition comprises a therapeutically or diagnostically effective amount of a single-domain antibody targeting PD-1 of claim 1, the humanized single-domain antibody targeting PD-1, the antibody targeting PD-1, the bispecific antibody, the fusion protein or the immunoconjugate, and optionally a pharmaceutically acceptable excipient.

* * * * *